US011485953B2

(12) United States Patent
Chang et al.

(10) Patent No.: US 11,485,953 B2
(45) Date of Patent: Nov. 1, 2022

(54) COMPOSITIONS AND METHODS FOR MAINTAINING CELL VIABILITY

(71) Applicant: Transwell Biotech Co., Ltd, Hsinchu (TW)

(72) Inventors: Ya-Hsuan Chang, Hsinchu (TW); Cheng-Yi Lin, Hsinchu (TW); Chih-Yuan Chao, Hsinchu (TW)

(73) Assignee: TRANSWELL BIOTECH CO., LTD., Hsinchu (CN)

( * ) Notice: Subject to any disclaimer, the term of this patent is extended or adjusted under 35 U.S.C. 154(b) by 589 days.

(21) Appl. No.: 15/723,872

(22) Filed: Oct. 3, 2017

(65) Prior Publication Data

US 2018/0094235 A1    Apr. 5, 2018

Related U.S. Application Data

(60) Provisional application No. 62/405,447, filed on Oct. 7, 2016, provisional application No. 62/404,170, filed on Oct. 4, 2016.

(51) Int. Cl.
*C12N 5/00* (2006.01)
*C12N 5/074* (2010.01)
*C12N 5/077* (2010.01)
*C12N 5/09* (2010.01)
*A01N 1/02* (2006.01)

(52) U.S. Cl.
CPC ......... *C12N 5/0018* (2013.01); *A01N 1/0221* (2013.01); *C12N 5/0068* (2013.01); *C12N 5/0607* (2013.01); *C12N 5/0656* (2013.01); *C12N 5/0693* (2013.01); *C12N 2533/54* (2013.01)

(58) Field of Classification Search
CPC .... C12N 5/00; C12N 2533/54; C12N 5/0018; C12N 5/0068; C12N 5/0607; C12N 5/0656; C12N 5/0693; A01N 1/0221
See application file for complete search history.

(56) References Cited

U.S. PATENT DOCUMENTS

| | | | |
|---|---|---|---|
| 6,673,607 B2 | 1/2004 | Toner et al. | |
| 7,094,601 B2 | 8/2006 | Toner et al. | |
| 8,420,307 B2 * | 4/2013 | Ostermeier | A01N 1/02 435/2 |
| 9,055,739 B2 | 6/2015 | Kato et al. | |
| 9,538,745 B2 | 1/2017 | He et al. | |
| 2009/0130756 A1 | 5/2009 | Klann et al. | |
| 2017/0196221 A1 | 7/2017 | Zhu et al. | |

FOREIGN PATENT DOCUMENTS

| | | |
|---|---|---|
| CN | 104630132 A | 5/2015 |
| EP | 0568726 A2 | 11/1993 |
| JP | H 06-234659 A | 8/1994 |
| JP | 2000506024 A | 5/2000 |
| JP | 2002-034552 A | 2/2002 |
| JP | 2007-289041 A | 11/2007 |
| JP | 2012-235728 A | 12/2012 |
| WO | WO-97/33975 | 9/1997 |
| WO | WO 0150851 A2 | 7/2001 |

OTHER PUBLICATIONS

Hubalek, Protectants Used in the cryopreservation of microorganisms, Cryobiology 46 (2003), p. 299 (Year: 2003).*
Zhang et al. 2006. Physiochemical properties of collagen, gelatin, and collagen hydrolysate derived from bovine limed split wastes, Journal of the Society of Leather technologists and chemists 90: 23-28 (Year: 2006).*
Santos et al. 2015. Evaluation of Different Methods of Cryopreservation of ehrlich tumor cells, Cryoletters 36(2): 68-73) (Year: 2015).*
Wu et al. 2013. Establishment and cryopreservation of a skin fibroblast cell line derived from Yunnan semi-fine wool sheep in the presence of synthetic ice blocker, CryoLetters 34(5):497-507 (Year: 2013).*
Lai et al. Effect of Charge and Molecular Weight on the Functionality of Gelatin Carriers for Corneal Endothelial Cell Therapy, Biomacromolecules 2006, 7, 1836-1844 (Year: 2006).*
Ohyabu et al. Evaluation of gelatin hydrogel as a potential carrier for cell transportation Journal of Bioscience and Bioengineering 2014118(1): 112-115 (Year: 2014).*
Supplementary European Search Report in corresponding European Application No. EP 17 85 7856, dated Mar. 18, 2020.
Second Non-Final Office Action in corresponding Taiwanese Application No. 106134216, dated Nov. 30, 2018.
Wang et al., "Cryopreservation of Cell/Hydrogel Constructs Based on a New Cell-assembling Technique" Journal of Bioactive and Compatible Polymers, vol. 25, Nov. 2010, p. 634-653.
Ishibashi et al., "Effectiveness of gelatin solidification for unfrozen preservation and transportation of astrocytes" Advances in Biological Chemistry, 2012, 2, 238-242.
International Preliminary Report on Patentability in corresponding PCT Application No. PCT/CN2017/105252, dated Apr. 9, 2019.
International Search Report and Written Opinion in corresponding PCT Application No. PCT/CN2017/105252, dated Jan. 15, 2018.
Lai JY, The role of bloom index of gelatin on the interaction with retinal pigment epithelial cells International Journal of Molecular Sciences Sep. 3, 2009(Sep. 3, 2009) No. 8 vol.10 ISSN:1422-0067 see the abstract, pp. 3444-3454.
Lopez-Urueña E, et al., The use of gelatin in long-term storage (up to 48 hr) at 5° C. preserves the pre-freezing and post-thawing quality of brown bear sperm Reproduction in Domestic Animals Jul. 14, 2016(Jul. 14, 2016) No. 5 vol. 51 ISSN:I439-0531.
Thompson et al., Cryopreservation and Thawing of Mammalian Cells, Dec. 2014, eLS, John Wiley & Sons, Ltd: Chichester. DOI: 0.1002/9780470015902.a0002561.pub2., pp. 1-7.
Cryobiology, 41 (4), pp. 257-279 (2000).
First Office Action of Japanese Patent Application No. 2019-517763, dated Apr. 26, 2021.
Wang, Xiaohong et al, "Incorporation of DMSO and dextran-40 into a gelatin/alginate hydrogel for controlled assembled cell cryopreservation," Cryobiology, 2010, vol. 61, pp. 345-351.

(Continued)

*Primary Examiner* — Taeyoon Kim
*Assistant Examiner* — Alexandra F Connors
(74) *Attorney, Agent, or Firm* — Leason Ellis LLP

(57) ABSTRACT

The present disclosure provides for a cell stabilizing medium which comprises gelatin. The cell stabilizing medium help maintain cell viability, e.g., after thawing of a biological material post-cryopreservation.

50 Claims, 5 Drawing Sheets

(56) References Cited

OTHER PUBLICATIONS

Wang, Xiaohong et al, "Cryopreservation of Cell/Hydrogel Constructs Based on a New Cell-assembling Technique," Journal of Bioactive and Compatible Polymers, 2010, vol. 25, pp. 634-653.
Katsen-Globa, Alisa et al., "Towards ready-to-use 3-D scaffolds for regenerative medicine: adhesion-based cryopreservation of human mesenchymal stem cells attached and spread within alginate-gelatin cryogel scaffolds," Journal of Materials Science: Materials in Medicine, 2014, vol. 25, pp. 857-871.
Lai, Jui-Yang, "The Role of Bloom Index of Gelatin on the Interaction with Retinal Pigment Epithelial Cells," International Journal of Molecular Sciences, 2009, vol. 10, pp. 3442-3456.
Santos, Kamilla M. et al., "Evaluation of Different Methods of Cryopreservation of Ehrlich Tumor Cells," CryoLetters, 2015, vol. 36, No. 2, pp. 68-73.
Wu, Shuai Shuai et al., "Establishment and Cryopreservation of a Skin Fibroblast Cell Line Derived From Yunnan Semi-Fine Wool Sheep in the Presence of Synthetic Ice Blocker," CryoLetters, 2013, vol. 34, No. 5, pp. 497-507.
Korean Office Action in corresponding Korean Application No. 10-2019-7009923, dated Jan. 24, 2022.
Xiaohong Wang, et al., "Incorporation of DMSO and dextran-40 into a gelatin/alginate hydrogel for controlled assembled cell cryopreservation," Cryobiology 61 (2010), pp. 345-351.
E Lopez-Urueña, et al, "The use of gelatine in long-term storage (up to 48 hr) at 5° C. preserves the pre-freezing and post-thawing quality of brown bear sperm," Wiley, Nov. 27, 2015, DOI: 10.1111/rda.12734, pp. 700-707.
Second Japanese Office Action in corresponding Japanese Application No. 2019-517763, dated Dec. 3, 2021 (with English translation).
Korean Second Office Action in corresponding Korean Application No. 10-2019-7009923, dated Jul. 27, 2022.
Xiaohong Wang, et al., "Cryopreservation of Cell/Hydrogel Constructs Based on a New Cell-assembling Technique," Journal of Bioactive and Compatible Polymers, vol. 25, Nov. 2010, pp. 634-653.

* cited by examiner

COMPOSITIONS AND METHODS FOR MAINTAINING CELL VIABILITY

CROSS REFERENCE TO RELATED APPLICATION

This application claims priority to U.S. Provisional Application Nos. 62/404,170 (filed on Oct. 4, 2016) and 62/405,447 (filed on Oct. 7, 2016), which are incorporated herein by reference in their entirety. This application is also related to International Application No. PCT/CN2017/105253, titled "Compositions and Methods for Cell Cryopreservation" and filed on Oct. 4, 2017, which is incorporated herein by reference in its entirety.

TECHNICAL FIELD

The present disclosure relates generally to the field of maintaining the viability of biological materials in vitro. In particular, the present disclosure relates to compositions and methods for maintaining the viability of biological materials such as cells and tissues when they are thawed after cryopreservation.

BACKGROUND OF THE DISCLOSURE

Cryopreservation techniques at temperatures at or below 0° C. are routinely used for long-time preservation of biological materials such as cells and tissues of animals (including human cells and tissues) and plants. Thompson et al., Cryopreservation and Thawing of Mammalian Cells, December 2014, eLS, John Wiley & Sons, Ltd: Chichester. DOI: 10.1002/9780470015902.a0002561.pub2. Effective long-term storage of mammalian cells is critical to the successful application of such cells as clinical and research tools. For example, stem cells can be used for cell transplantation, tissue engineering, and regenerative medicine. Cryopreserved oocytes, sperm, and embryos can be used in assisted reproductive technologies. In transplantation medicine, living tissues such as the skin, cornea, pancreatic islets and heart valves need to be cryopreserved.

Cells can be stored at subzero temperatures (e.g., below −70° C.) for months or years. However, cells are not stable when and after they are thawed. The stability, mainly indicated by the viability, of the cells, varies with the environment with which the cells contact during and after the thawing process. It has been shown that the thawing rate, osmotic stress, and cryoprotectant toxicity would damage cells after thawing. Thompson et al., Cryopreservation and Thawing of Mammalian Cells, December 2014, eLS, John Wiley & Sons, Ltd: Chichester. DOI: 10.1002/9780470015902.a0002561.pub2. If the cells will be injected into a subject (e.g., through cell therapy, blood transfusion, or bone marrow transplantation etc.), it is very important to obtain a high cell viability after thawing, as it can be futile to reinject dead or damaged cells. Likewise, when cells have to be re-cultured, it is equally important that the cell viability is high.

How to maintain cell viability as they are transitioned from a cryogenic state to a metabolically active state is a challenging task. Thus, there is a need for improved media and methods for maintaining cell viability after thawing.

SUMMARY

The present disclosure provides for a cell stabilizing medium comprising about 5 wt % to about 15.7 wt %, about 5 wt % to about 7.5 wt %, about 10 wt % to about 15.7 wt %, about 0.8 wt % to about 15.7 wt %, about 2.4 wt % to about 7 wt %, or about 9.3 wt % to about 14.6 wt %, of gelatin (based on the total weight of the cell stabilizing medium).

Also encompassed by the present disclosure is a composition comprising a biological material (e.g., one or more cells, a tissue(s), an organ(s), and/or viral particles) and about 0.8 wt % to about 15.7 wt %, about 2.4 wt % to about 7 wt %, or about 9.3 wt % to about 14.6 wt %, of gelatin.

In certain embodiments, the biological material (e.g., one or more cells, a tissue(s), an organ(s), and/or viral particles) have been thawed from a cryopreserved state. In certain embodiments, the cells have a post-thaw viability of at least 70%, or at least 80%.

The present disclosure provides for a method for maintaining viability of a biological material (e.g., cell viability), the method comprising the step of: mixing a biological material (e.g., one or more cells, a tissue(s), an organ(s), and/or viral particles) with a cell stabilizing medium to form a mixture (or to form a combination of the cell stabilizing medium and the biological material (e.g., one or more cells, a tissue(s), an organ(s), and/or viral particles)).

The present disclosure provides for a method for maintaining cell viability, the method comprising the step of: mixing one or more cells with a cell stabilizing medium to form a mixture (or a combination of the cell stabilizing medium and the biological material (e.g., one or more cells, a tissue(s), an organ(s), and/or viral particles)), where the mixture (or combination) comprises about 0.8 wt % to about 15.7 wt %, about 2.4 wt % to about 7 wt %, or about 9.3 wt % to about 14.6 wt %, of gelatin.

In certain embodiments, the one or more cells are in a cell suspension before the mixing step.

In certain embodiments, for the mixing step, the volume ratio of the cell stabilizing medium to the cell suspension ranges from about 6.25 to about 12.5, or from about 5 to about 10.

In certain embodiments, the cells are in the cell suspension at a concentration ranging from about $7.5 \times 10^5$ cells/ml to about $7.5 \times 10^7$ cells/ml.

In certain embodiments, the method further comprises placing the cell stabilizing medium at a temperature ranging from about 25° C. to about 37° C. before the mixing step.

In certain embodiments, before the mixing step, the one or more cells are in a cryopreservation composition which has been thawed from a cryopreserved state. In certain embodiments, the cryopreserved state is at a temperature ranging from about −70° C. and −200° C.

In certain embodiments, the cells have a post-thaw viability of at least 70%, or at least 80%.

In certain embodiments, the cryopreservation composition comprises glycerol, dimethyl sulfoxide (DMSO), and/or polyethylene glycol (PEG).

In certain embodiments, after the mixing step, the cells are present in the mixture at a concentration ranging from about $10^5$ cells/ml to about $10^7$ cells/ml.

In certain embodiments, gelatin has a weight average molecular mass (or molecular weight, or average molecular weight) ranging from about 100 kilodalton (kD) to about 200 kD. In certain embodiments, gelatin comprises denatured collagen. In certain embodiments, the cell stabilizing medium is a thermoreversible hydrogel having a bloom value ranging from about 190 to about 325.

In certain embodiments, the cells are mammalian cells. In certain embodiments, the cells are human, porcine, canine, equine or bovine cells. In certain embodiments, the cells comprise tumor cells. In certain embodiments, the cells comprise fibroblasts. In certain embodiments, the cells comprise stem cells.

In certain embodiments, the cell stabilizing medium further comprises an amino acid, a cytokine, a lipid, a growth factor, an antibiotic, an antimycotic, a steroid hormone, a protein hormone, or a combination thereof.

The present disclosure provides for a kit comprising the present composition or the present cell stabilizing medium.

DETAILED DESCRIPTION OF THE INVENTION

Figure 1:
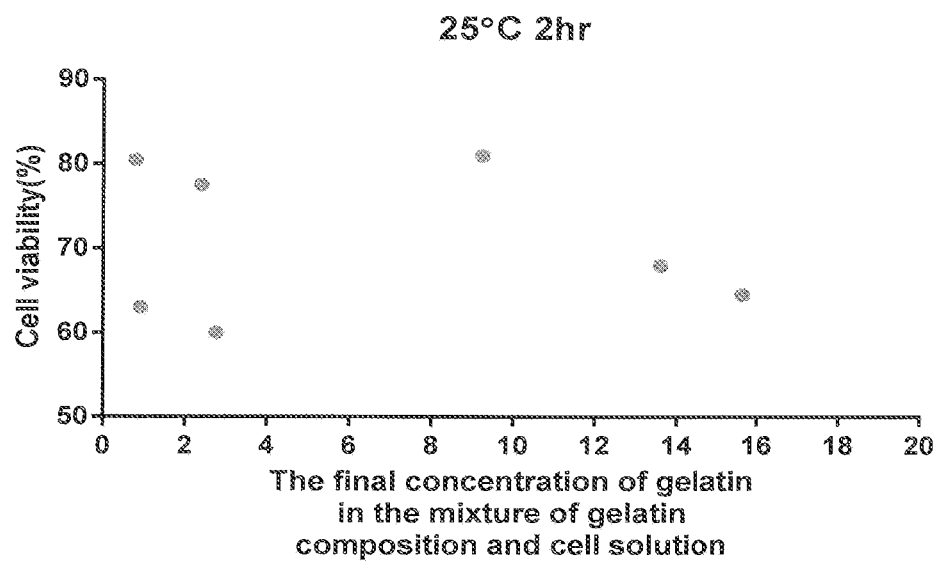
FIG. 1 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. The mixture was incubated at 25° C. for 2 hours before post-thaw cell viabilities were assayed.

The present disclosure provides for a cell stabilizing medium which comprises, e.g., gelatin. The cell stabilizing medium help maintain cell viability, e.g., after thawing of a biological material post-cryopreservation. By mixing with the present cell stabilizing medium, the viability of the cells can be maintained for a desirable time.

The biological material (e.g., cells) can then be used in a variety of research and clinical settings, for example, for cell-based therapeutics, in assisted reproductive technology, or for patients undergoing chemotherapy or radiation therapy. In one embodiment, the biological material may be administered to a subject.

In certain embodiments, the biological material (e.g., cells, tissues, organs, or viral particles) is thawed (or has been thawed) from cryopreservation (from a cryopreserved state). In certain embodiments, the biological material has been under cryopreservation. In certain embodiments, while being mixed with the cell stabilizing medium, the biological material is in the process of being thawed from, or has been thawed from, cryopreservation. In certain embodiments, after being combined/mixed with the present cell stabilizing medium, the cells have a post-thaw viability of at least about 50%, at least about 60%, at least about 70%, at least about 75%, at least about 80%, at least about 85%, at least about 90%, or at least about 95%.

In certain embodiments, when the biological material (e.g., cells, tissues, organs, or viral particles) is thawed (or has been thawed) from cryopreservation, the biological material is in a cryopreservation composition which comprises one or more permeating cryoprotectants, and/or one or more non-permeating cryoprotectants. Non-limiting examples of permeating cryoprotectants include glycerol, DMSO, polyethylene glycol, ethylene glycol, and propylene glycol (1,2-propanediol, propane-1,2-diol). Non-limiting examples of non-permeating cryoprotectants include high molecular weight molecules, such as saccharides (e.g., sucrose, trehalose, maltose), sugars, starches (e.g., hydroxyethyl starch), protein (e.g., albumin such as serum albumin), percoll, ficol, polyethylene glycol, dextran, polyvinyl pyrrolidone, polyvinylalcohol (PVA), serum, plasma and other macromolecules. In certain embodiments, the cryopreservation composition comprises one or more cryoprotectants including, but not limited to, glycerol, dimethyl sulfoxide (DMSO), and/or polyethylene glycol (PEG).

As used herein, the term "cryopreserved state" means a state of being at a cryopreserved temperature.

In specific embodiments, a cryopreservation temperature comprises a temperature of at or below about 0° C., at or below about −20° C., at or below about −50° C., at or below about −60° C., at or below about −70° C., at or below about −80° C., at or below about −90° C., at or below about −100° C., at or below about −110° C., at or below about −120° C., at or below about −135° C., at or below about −196° C., from about −70° C. to about −200° C., or in liquid nitrogen.

In certain embodiments, the biological material (e.g., cells, tissues, organs, or viral particles) is in a hypothermic preserved state before being combined/mixed with the cell stabilizing medium. In certain embodiments, the biological material (cells, tissues, organs) was in a lyophilized state before being combined/mixed with the cell stabilizing medium.

In certain embodiments, the cells are under cell culture before being combined/mixed with the cell stabilizing medium. Cells may be harvested at sub-confluence, at the exponential growth phase, at confluence, or post-confluence.

In certain embodiments, the cells are harvested from a subject (e.g., a patient) before being combined/mixed with the cell stabilizing medium.

In certain embodiments, after being combined/mixed with the present cell stabilizing medium, the cells have a viability of at least about 50%, at least about 60%, at least about 70%, at least about 75%, at least about 80%, at least about 85%, at least about 90%, or at least about 95%.

In certain embodiments, the cells comprise tumor cells. In certain embodiments, the cells comprise fibroblasts. In certain embodiments, the cells comprise stem cells.

In certain embodiments, the cells comprise mammalian cells, including, but not limited to, human, porcine, canine, equine or bovine cells.

In certain embodiments, the present method may further comprise the step of administering to a subject (e.g., a patient) the biological material treated with the present cell stabilizing medium.

In certain embodiments, the cell stabilizing medium comprises about 5 wt % to about 15.7 wt % of gelatin (based on the total weight of the cell stabilizing medium). In certain embodiments, the cell stabilizing medium comprises about 2 wt % to about 20 wt %, about 3 wt % to about 18 wt %, about 4 wt % to about 17 wt %, about 5 wt % to about 16 wt %, about 5 wt % to about 15.7 wt %, about 5 wt % to about 7.5 wt %, about 10 wt % to about 15.7 wt %, about 5 wt % to about 6 wt %, about 6 wt % to about 7.5 wt %, about 7.5 wt % to about 10 wt %, about 5 wt % to about 10 wt %, about 6 wt % to about 7.5 wt %, about 6 wt % to about 10 wt %, about 6 wt % to about 15.7 wt %, about 7.5 wt % to about 10 wt %, about 7.5 wt % to about 15.7 wt %, about 5 wt %, about 6 wt %, about 7.5 wt %, about 10 wt %, or about 15.7 wt %, of gelatin based on the total weight of the cell stabilizing medium.

In certain embodiments, the cell stabilizing medium comprises (or consists of, or consists essentially of) about 5 wt % to about 15.7 wt % of gelatin, and a solvent (e.g., a culture medium such as DMEM, water, a buffer, a saline solution etc.). In certain embodiments, the cell stabilizing medium comprises (or consists of, or consists essentially of) an aqueous gelatin solution where the concentration of gelatin ranges from about 5 wt % to about 15.7 wt %.

In certain embodiments, the cell stabilizing medium comprises (or consists of, or consists essentially of) about 5 wt % to about 15.7 wt % of gelatin, and a buffer system (e.g., a physiological buffer). In certain embodiments, the cell stabilizing medium comprises (or consists of, or consists essentially of) about 5 wt % to about 15.7 wt % of gelatin, and a salt solution, and/or any physiological solution.

In certain embodiments, the cell stabilizing medium comprises (or consists of, or consists essentially of) about 5 wt % to about 15.7 wt % of gelatin, and a culture medium (e.g., a cell culture medium).

In certain embodiments, in the present cell stabilizing medium, gelatin is mixed with a liquid composition. In certain embodiments, the cell stabilizing medium comprises (or consists of, or consists essentially of) about 5 wt % to about 15.7 wt % of gelatin, and a liquid composition. Non-limiting examples of liquid compositions include water, a culture medium, a mixture of culture media, a buffer system (e.g., a physiological buffer), a salt solution, and/or any physiological solution. In certain embodiments, the liquid composition further comprises supplements, additives, additional amounts of some medium components, etc.

In certain embodiments, the cell stabilizing medium comprises (or consists of, or consists essentially of) two constituents: the first constituent being gelatin which is present in the cell stabilizing medium at a concentration ranging from about 5 wt % to about 15.7 wt %; the second constituent being a saline solution (e.g., an isotonic saline solution), a buffer system (e.g., a physiological buffer), water, and/or a culture medium (e.g., a cell culture medium).

The present disclosure provides for a method for maintaining the viability of a biological material (e.g., cell viability). The method may comprise the step of mixing a biological material (e.g., cells, tissues, organs, or viral particles) with a cell stabilizing medium to form a mixture. In certain embodiments, the cell stabilizing medium comprises about 5 wt % to about 15.7 wt % of gelatin based on the total weight of the cell stabilizing medium.

The biological material (e.g., cells, tissues, organs, or viral particles) can be combined with the present cell stabilizing medium by any suitable method. In certain embodiments, the cell stabilizing medium is added to the biological material. In certain embodiments, the biological material is added to the cell stabilizing medium. In one embodiment, the method comprises providing cells in a cell suspension, and adding the cell stabilizing medium to the cell suspension, optionally with mixing. In another embodiment, the method comprises providing cells in a cell suspension, and adding the cell suspension to the cell stabilizing medium, optionally with mixing.

In certain embodiments, cells are freed of their culture medium or preservation medium (e.g., centrifuged, harvested, and optionally washed in a buffer solution), before being combined/mixed with the present cell stabilizing medium.

In certain embodiments, before mixing the cells and the present cell stabilizing medium, the cells are in a cell suspension. In certain embodiments, the cells are suspended in a culture medium (e.g., a cell culture medium), a buffer system (e.g., a physiological buffer), a salt solution, and/or a physiological solution.

In certain embodiments, the cells are present in the cell suspension at a concentration ranging from about $10^4$ cells/ml to about $10^9$ cells/ml, from about $10^4$ cells/ml to about $10^8$ cells/ml, from about $7.5\times10^5$ cells/ml to about $7.5\times10^7$ cells/ml, from about $5\times10^5$ cells/ml to about $5\times10^7$ cells/ml, from about $8\times10^5$ cells/ml to about $7.5\times10^7$ cells/ml, from about $9\times10^5$ cells/ml to about $7.5\times10^7$ cells/ml, from about $10^6$ cells/ml to about $7.5\times10^7$ cells/ml, from about $5\times10^6$ cells/ml to about $7.5\times10^7$ cells/ml, from about $7.5\times10^6$ cells/ml to about $7.5\times10^7$ cells/ml, from about $7.5\times10^5$ cells/ml to about $7.5\times10^6$ cells/ml, from about $10^5$ cells/ml to about $10^7$ cells/ml, from about $10^5$ cells/ml to about $10^8$ cells/ml, from about $10^4$ cells/ml to about $10^7$ cells/ml, about $7.5\times10^5$ cells/ml, about $7.5\times10^6$ cells/ml, or about $7.5\times10^7$ cells/ml, about $10^5$ cells/ml, about $10^6$ cells/ml, or about $10^7$ cells/ml. In certain embodiments, the cells are present in the cell suspension at a concentration ranging from about $7.5\times10^5$ cells/ml to about $7.5\times10^7$ cells/ml. In certain embodiments, the cells are present in the cell suspension at a concentration of about $7.5\times10^6$ cells/ml. The concentration of the cells in the cell suspension may be higher than $10^9$ cells/ml or lower than $10^4$ cells/ml.

In certain embodiments, the cells and the present cell stabilizing medium are mixed to form a mixture.

The present disclosure provides for a method for maintaining cell viability. The method may comprise the step of mixing one or more cells with a cell stabilizing medium to form a mixture. In certain embodiments, the mixture comprises about 0.8 wt % to about 15.7 wt % of gelatin.

In certain embodiments, the mixture of cells (which may or may not be in a cell suspension) and the present cell stabilizing medium, (or the combination of a biological material and the cell stabilizing medium) comprises about 0.8 wt % to about 15.7 wt % of gelatin (based on the total weight of the mixture). In certain embodiments, the mixture (or the combination) comprises about 0.5 wt % to about 20 wt %, about 0.6 wt % to about 18 wt %, about 0.7 wt % to about 17 wt %, about 0.8 wt % to about 16 wt %, about 0.8 wt % to about 15.7 wt %, about 0.5 wt % to about 15.7 wt %, about 1 wt % to about 17 wt %, about 2 wt % to about 14 wt %, about 3 wt % to about 9.5 wt %, about 4 wt % to about 14 wt %, about 2.4 wt % to about 7 wt %, about 9.3 wt % to about 14.6 wt %, about 5 wt % to about 7.5 wt %, about 10 wt % to about 15.7 wt %, about 5 wt % to about 6 wt %, about 6 wt % to about 7.5 wt %, about 7.5 wt % to about 10 wt %, about 5 wt % to about 10 wt %, about 6 wt % to about 7.5 wt %, about 6 wt % to about 10 wt %, about 6 wt % to about 15.7 wt %, about 7.5 wt % to about 10 wt %, about 7.5 wt % to about 15.7 wt %, about 5 wt %, about 6 wt %, about 7.5 wt %, about 10 wt %, or about 15.7 wt %, of gelatin based on the total weight of the mixture (or the combination).

In certain embodiments, the cells and the present cell stabilizing medium are mixed to form a mixture, where the cells are present in the mixture at a concentration ranging from about $10^4$ cells/ml to about $10^9$ cells/ml, from about $10^4$ cells/ml to about $10^8$ cells/ml, from about $10^5$ cells/ml to about $10^7$ cells/ml, from about $10^6$ cells/ml to about $10^7$ cells/ml, from about $10^5$ cells/ml to about $10^6$ cells/ml, from about $10^5$ cells/ml to about $10^8$ cells/ml, from about $10^4$ cells/ml to about $10^7$ cells/ml, about $10^5$ cells/ml, about $10^6$ cells/ml, or about $10^7$ cells/ml. In certain embodiments, the cells are present in the mixture at a concentration ranging from about $10^5$ cells/ml to about $10^7$ cells/ml. In certain embodiments, the cells are present in the mixture at a concentration of about $10^6$ cells/ml. The concentration of the cells in the mixture may be higher than $10^9$ cells/ml or lower than $10^4$ cells/ml.

In certain embodiments, for the mixing step, the volume ratio of the cell stabilizing medium to the cell suspension (or a composition containing the biological material) ranges from about 3 to about 25, from about 5 to about 20, from about 6 to about 18, from about 6 to about 15, from about 6.25 to about 12.5, from about 7 to about 12.5, from about 6.25 to about 15, from about 6.25 to about 20, from about 8 to about 12.5, from about 9 to about 12.5, from about 5 to about 12.5, from about 5 to about 10, from about 5 to about 8, about 5, about 6, about 6.25, about 7, about 8, about 9, about 10, about 11, about 12, about 12.5, about 13, about 14, or about 15.

In certain embodiments, the viability of the cells in the mixture of a biological material (such as cells which may or may not be in a cell suspension) and the present cell stabilizing medium is reduced less than about 40%, less than about 30%, less than about 20%, less than about 10%, less than about 9%, less than about 8%, less than about 7%, less than about 6%, less than about 5%, less than about 4%, less than about 3%, or less than about 1%, after the mixture is incubated at a temperature of about 25° C., about 27° C., about 30° C., or about 37° C., for a time period ranging from about 1 hour to about 8 hours, from about 2 hours to about 8 hours, from about 3 hours to about 8 hours, from about 2 hours to about 4 hours, from about 1 hour to about 6 hours, from about 4 hours to about 8 hours, from about 1 hour to about 5 hours, from about 1 hour to about 4 hours, from about 1 hour to about 3 hours, from about 1 hour to about 2 hours, from about 2 hours to about 4 hours, from about 2 hours to about 3 hours, from about 3 hours to about 5 hours, from about 5 minutes to about 20 minutes, from about 5 minutes to about 30 minutes, from about 10 minutes to about 1 hour, from about 20 minutes to about 1 hour, about 30 minutes, about 1 hour, about 2 hours, about 3 hours, about 4 hours, about 5 hours, about 6 hours, about 7 hours, or about 8 hours.

In certain embodiments, the viability of the cells in the mixture of a biological material (such as cells which may or may not be in a cell suspension) and the present cell stabilizing medium is at least about 50%, at least about 60%, at least about 70%, at least about 75%, at least about 80%, at least about 85%, at least about 90%, or at least about 95%, after the mixture is incubated at a temperature of about 25° C., about 27° C., about 30° C., or about 37° C., for a time period ranging from about 1 hour to about 8 hours, from about 2 hours to about 8 hours, from about 3 hours to about 8 hours, from about 2 hours to about 4 hours, from about 1 hour to about 6 hours, from about 4 hours to about 8 hours, from about 1 hour to about 5 hours, from about 1 hour to about 4 hours, from about 1 hour to about 3 hours, from about 1 hour to about 2 hours, from about 2 hours to about 4 hours, from about 2 hours to about 3 hours, from about 3 hours to about 5 hours, from about 5 minutes to about 20 minutes, from about 5 minutes to about 30 minutes, from about 10 minutes to about 1 hour, from about 20 minutes to about 1 hour, about 30 minutes, about 1 hour, about 2 hours, about 3 hours, about 4 hours, about 5 hours, about 6 hours, about 7 hours, or about 8 hours.

The present disclosure provides for a composition comprising a biological material (e.g., one or more cells, tissues, organs) and about 0.8 wt % to about 15.7 wt % of gelatin. In certain embodiments, the composition comprises about 0.8 wt % to about 15.7 wt % of gelatin (based on the total weight of the composition). In certain embodiments, the composition comprises about 0.5 wt % to about 20 wt %, about 0.6 wt % to about 18 wt %, about 0.7 wt % to about 17 wt %, about 0.8 wt % to about 16 wt %, about 0.8 wt % to about 15.7 wt %, about 0.5 wt % to about 15.7 wt %, about 1 wt % to about 17 wt %, about 2 wt % to about 14 wt %, about 3 wt % to about 9.5 wt %, about 4 wt % to about 14 wt %, about 2.4 wt % to about 7 wt %, about 9.3 wt % to about 14.6 wt %, about 5 wt % to about 7.5 wt %, about 10 wt % to about 15.7 wt %, about 5 wt % to about 6 wt %, about 6 wt % to about 7.5 wt %, about 7.5 wt % to about 10 wt %, about 5 wt % to about 10 wt %, about 6 wt % to about 7.5 wt %, about 6 wt % to about 10 wt %, about 6 wt % to about 15.7 wt %, about 7.5 wt % to about 10 wt %, about 7.5 wt % to about 15.7 wt %, about 5 wt %, about 6 wt %, about 7.5 wt %, about 10 wt %, or about 15.7 wt %, of gelatin based on the total weight of the composition.

In certain embodiments, the biological material (e.g., cells, tissues, organs, or viral particles) is thawed (or has been thawed) from cryopreservation (a cryopreserved state). In certain embodiments, the biological material has been under cryopreservation. In certain embodiments, the biological material is in the process of being thawed from, or has been thawed from, cryopreservation.

The present cell stabilizing medium may be a liquid or a solid. In certain embodiments, the present cell stabilizing medium is a concentrate composition, such as, in a dry form (e.g., powder, tablet, granular or any other suitable physical form) or in liquid form as, e.g., 2×, 3×, 4×, 5×, 6×, 7×, 8×, 9×, 10×, 15×, 20× etc. stock solutions. The stock solutions can be diluted 2×, 3×, 4×, 5×, 6×, 7×, 8×, 9×, 10×, 15×, 20× etc. by, e.g., a culture medium, a physiologic solution, a buffer, water etc. the dry form of the cell stabilizing medium may be converted to a liquid form by adding, e.g., a culture medium, a physiologic solution, a buffer, water etc. (e.g., dissolved in, e.g., a culture medium, a physiologic solution, a buffer, water etc.).

In certain embodiment, the concentrations of the components discussed herein are the concentrations of the components in a stock solution of the present cell stabilizing medium. In certain embodiment, the concentrations of the components discussed herein are the concentrations of the components in a working solution of the present cell stabilizing medium.

The present cell stabilizing medium may be a solution. In certain embodiments, the cell stabilizing medium is an aqueous solution of the components discussed herein.

In certain embodiments, when preparing the present cell stabilizing medium, the components discussed herein (e.g., gelatin, a gelatin derivative, and/or albumin) are dissolved in a balanced electrolyte solution (e.g., a saline solution, a culture medium such as a cell culture medium). In certain embodiments, the cell stabilizing medium has an appropriate concentration of electrolytes (such as sodium, potassium, and/or chloride ions) to maintain a normal osmolality. In one embodiment, the saline solution is a phosphate-buffered saline solution (PBS). In one embodiment, the saline solution comprises one or more of the following: Sodium Chloride, Potassium Chloride, Magnesium Sulfate, Potassium Phosphate, Calcium Chloride, and Sodium Bicarbonate. In one embodiment, the saline solution is an isotonic saline solution (e.g., isotonic with the plasma, or a body fluid).

The present cell stabilizing medium may comprise a buffer system (e.g., a physiological buffer). The present cell stabilizing medium may comprise a balanced salt solution or any physiological solution.

Non-limiting examples of the buffer systems include phosphoric acid buffers (for example, phosphate buffered saline (PBS)), BES, TES, acetamidoglycine, glycine amides, glycylglycine, TRICINE, TALP, tris-ethanolamine, veronal, and HEPES.

In certain embodiments, the concentration of the buffer in the present cell stabilizing medium ranges from about 1 mM to about 1000 mM, from about 1 mM to about 200 mM, from about 5 mM to about 200 mM, or from about 5 mM to about 50 mM.

Non-limiting examples of culture media include, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, RPMI 1640 Media, and combinations thereof and/or modifications thereof. In one embodiment, the cell culture is DMEM.

In certain embodiments, the present cell stabilizing medium has a pH ranging from about 6.0 to about 8.5, from about 6.5 to about 8, from about 6.9 to about 7.5, or from about 7.2 to about 7.4 at room temperature or ambient temperature (for example, at 25° C.).

In certain embodiments, the cell stabilizing medium is packaged in unit forms. In one embodiment, the cell stabilizing medium is packaged in a volume of 10 ml, 50 ml, 100 ml, 500 ml or 1 L. In certain embodiments, the cell stabilizing medium is packaged as a 1×, 5×, 10×, or 20× solution.

The present cell stabilizing medium can be obtained in a solid form by mixing the components discussed herein, or as an aqueous solution by dissolving the components in water, a buffer, a solution, a culture medium, etc.

As used herein, the percentage "% (w/v)" is percent weight to volume (w in gram and v in milliliter); the percentage "% (v/v)" is percent volume to volume; the percentage "% (w/w)" or "wt %" is percent weight to weight.

The term "about" in reference to a numeric value refers to ±10% of the stated numeric value. In other words, the numeric value can be in a range of 90% of the stated value to 110% of the stated value.

Gelatin

The present cell stabilizing medium may comprise a gelatin and/or a gelatin derivative. As used herein, the term "gelatin" may refer to gelatin or a gelatin derivative. Any gelatin or a gelatin derivative may be used in the present cell stabilizing medium.

In certain embodiments, gelatin in the present cell stabilizing medium has a molecular weight (or weight average molecular mass, or average molecular mass) ranging from about 15 kilodalton (kD) to about 40 kD, from about 25 kD to about 40 kD, from about 25 kD to about 50 kD, from about 25 kD to about 45 kD, from about 40 kD to about 50 kD, from about 10 kD to about 100 kD, from about 40 kD to about 100 kD, from about 50 kD dalton to about 100 kD, from about 100 kD to about 200 kD, from about 100 kD to about 250 kD, from about 80 kD to about 200 kD, from about 150 kD to about 200 kD, from about 100 kD to about 150 kD, or from about 50 kD to about 200 kD.

In certain embodiments, gelatin in the present cell stabilizing medium has an isoelectric point (pI) ranging from about 4.5 to about 9, from about 5 to about 9, from about 5 to about 7, from about 6 to about 7, from about 5 to about 6, from about 7 to about 9, or from about 4.7 to about 5.2.

In certain embodiments, gelatin is derived from mammalian tissue. In certain embodiments, gelatin is obtained from animal collagen. In certain embodiments, gelatin is derived from raw materials including, but not limited to, the skin, bones, connective tissues, tendons, ligaments, etc. of animals such as cattle, chicken, pigs, and fish. In one embodiment, gelatin is of bovine source, porcine source, or a combination thereof. In certain embodiments, gelatin is sourced from bovine bones and porcine skin, bovine skin, pork, bovine hides, and/or fish skin. In one embodiment, gelatin is skin-derived gelatin or bone-derived gelatin.

In certain embodiments, gelatin is a mixture of peptides and proteins produced by partial hydrolysis of collagen. In certain embodiments, gelatin is a hydrolyzed form of collagen. In certain embodiments, gelatin is a form of denatured collagen. In certain embodiments, gelatin comprises denatured collagen.

In certain embodiments, gelatin may be type A gelatin or type B gelatin. As used herein, type A gelatin is the gelatin obtained from acid-treated raw material; type B gelatin is the gelatin obtained from alkali-treated raw material.

In certain embodiments, to produce gelatin, collagen hydrolysis is performed by chemical hydrolysis, and/or thermal hydrolysis. In one embodiment, collagen is boiled (e.g., in water) or heated (extensively) to produce gelatin.

In certain embodiments, to produce gelatin, collagen hydrolysis is performed by acid-hydrolysis, alkali-hydrolysis, and/or enzymatic hydrolysis.

In certain embodiments, the manufacturing processes of gelatin contain three main stages: the pretreatment, the main extraction step, and the refining and recovering treatments. Pretreatments make the raw materials ready for the main extraction step and remove impurities that may have negative effects on physiochemical properties of the final gelatin product. The main extraction step may be done with hot water or dilute acid solutions as a multistage extraction to hydrolyze collagen into gelatin. The refining and recovering treatments include filtration, clarification, evaporation, sterilization, drying, rutting, grinding, and/or sifting to remove the water from the gelatin solution, to blend the gelatin extracted, and/or to obtain dried, blended and ground final product.

In certain embodiments, the present cell stabilizing medium comprises fractionated gelatin which is obtained from conventional gelatin by special preparation techniques, such as ultrafiltration. In certain embodiments, fractionated gelatin is obtained by removal of a selected portion(s) of peptides/polypeptides, or by mixtures of individual fractions of peptides/polypeptides.

Gelatin derivatives are chemically modified gelatins, including, but not limited to, succinylated gelatin, thiolated gelatin, acetylated gelatin, phthalated gelatin, succinyl gelatin, oxypolygelatin, or urea cross-linked gelatin. In one embodiment, succinylated gelatin is a gelatin cross-linked by succinic acid or its salt, or succinic anhydride. In certain embodiments, a gelatin derivative is obtained by reacting gelatin with an anhydride, such as succinic, citraconic, itaconic, aconitic or maleic anhydride. U.S. Pat. Nos. 8,865,397 and 6,103,269.

Polypeptides

The present cell stabilizing medium may contain any suitable polypeptide. In certain embodiments, the cell stabilizing medium comprises a polypeptide component and a liquid component.

A polypeptide, as used herein, is intended to encompass any tissue-derived or synthetically produced polypeptide, such as collagen-derived components (such as gelatin). In specific embodiments, a polypeptide can comprise (or consists of) from about 50 amino acid residues to about 30,000 amino acid residues, preferably about 100 amino acid residues to about 20,000 amino acid residues, more preferably about 200 amino acid residues to about 10,000 amino acid residues, still more preferably about 300 amino acid residues to about 5,000 amino acid residues, and most preferably about 500 amino acid residues to about 2,000 amino acid residues.

In certain embodiments, the polypeptide comprises gelatin, albumin, or a combination thereof.

In certain embodiments, the polypeptide is gelatin or a gelatin derivative (e.g., succinylated gelatin). In certain embodiments, the polypeptide is other gelatin-like components, such as keratin, decorin, aggrecan, elastin, laminin, nidogen, fibulin, fibrillin, collagen, fractionated gelatin, collagen hydrolyzates, plant proteins, plant protein hydrolyzates, elastin hydrolyzates, glycoproteins (including proteoglycans), and mixtures thereof.

Polypeptides derived from other types of tissue could also be used. Examples include, but are not limited to, tissue extracts from arteries, vocal chords, pleura, trachea, bronchi, pulmonary alveolar septa, ligaments, auricular cartilage or abdominal fascia; the reticular network of the liver; the basement membrane of the kidney; or the neurilemma, arachnoid, dura mater or pia mater of the nervous system. The polypeptide may comprise natural components, and/or synthetic components. Examples of natural components include, but are not limited to, naturally occurring proteins and polypeptides.

In certain embodiments, the cell stabilizing medium comprises about 2 wt % to about 20 wt %, about 3 wt % to about 18 wt %, about 4 wt % to about 17 wt %, about 5 wt % to about 16 wt %, about 5 wt % to about 15.7 wt %, about 5 wt % to about 7.5 wt %, about 10 wt % to about 15.7 wt %, about 5 wt % to about 6 wt %, about 6 wt % to about 7.5 wt %, about 7.5 wt % to about 10 wt %, about 5 wt % to about 10 wt %, about 6 wt % to about 7.5 wt %, about 6 wt % to about 10 wt %, about 6 wt % to about 15.7 wt %, about 7.5 wt % to about 10 wt %, about 7.5 wt % to about 15.7 wt %, about 5 wt %, about 6 wt %, about 7.5 wt %, about 10 wt %, or about 15.7 wt %, of one or more polypeptides (as discussed herein) based on the total weight of the cell stabilizing medium.

Albumin

Any albumin or an albumin derivative may be used in the present cell stabilizing medium.

Non-limiting examples of albumin include serum albumin (e.g., human serum albumin or HSA), plasma albumin (e.g., human plasma albumin), bovine serum albumin, and/or synthetic serum albumin), ovalbumin, plant albumin, or combinations thereof. Non-limiting examples of albumin also include fetal bovine serum.

Albumin may be either of natural origin (e.g., purified from a natural source) or of recombinant origin (recombinant albumin). In one embodiment, albumin is produced by purification from biological material of human origin. It may be obtained by conventional techniques for fractionation of plasma obtained from blood (Cohn et al., J. Am. Chem. Soc. 68 (1946) 459 pp), or by extraction from the human placenta, according to the technique described by J. Liautaud et al. (13th International IABS Conference, Budapest; A: "Purification of proteins. Development of biological standard", Karger (ed.), Bale, 27 (1973) 107 pp). In one embodiment, recombinant albumin is produced in a eukaryotic host.

In one embodiment, the term "albumin" comprises any natural variant of human albumin, resulting from the polymorphism of this protein.

Hydrogels

In certain embodiments, the present cell stabilizing medium is a hydrogel. In certain embodiments, the present cell stabilizing medium is a thermoreversible hydrogel, which undergoes a transition from a flowable state (a liquid state) to a gel state in response to a change in temperature. In certain embodiments, the present cell stabilizing medium is in a free flowing or liquid phase at or above a phase transition temperature, and is in a gel phase (a solid phase, a non-flowable phase) below a phase transition temperature. U.S. Pat. Nos. 6,231,881 and 6,730,315.

In certain embodiments, the present cell stabilizing medium has a fluid phase (e.g., a gelatin solution) above a phase transition temperature and has a gel phase (e.g., a gelatin hydrogel) at or below the phase transition temperature. In certain embodiments, the conversion between the fluid phase and the gel phase is a continuous process. In certain embodiments, in the gel phase, the extent of the gelation of the cell stabilizing medium provides an operable hydrogel. In certain embodiments, the phase transition temperature can also be a critical temperature at which the viscosity of the cell stabilizing medium ensures that the cell stabilizing medium is an operable hydrogel. In certain embodiments, the phase transition temperature is the melting point.

In certain embodiments, the cell stabilizing medium has a phase transition temperature ranging from about 20° C. to about 45° C., from about 20° C. to about 40° C., from about 21° C. to about 39° C., from about 22° C. to about 38° C., from about 23° C. to about 37° C., from about 25° C. to about 37° C., from about 28° C. to about 37° C., from about 30° C. to about 37° C., from about 32° C. to about 37° C., above about 37° C., or about 37° C.

In certain embodiments, the cell stabilizing medium in its liquid phase is combined/mixed with a biological material (e.g., cells, tissues, organs, viral particles etc.) to form a mixture.

In certain embodiments, the cell stabilizing medium is placed at a temperature ranging from about 20° C. to about 45° C., from about 20° C. to about 40° C., from about 21° C. to about 39° C., from about 22° C. to about 38° C., from about 23° C. to about 37° C., from about 25° C. to about 37° C., from about 28° C. to about 37° C., from about 30° C. to about 37° C., from about 32° C. to about 37° C., above about 37° C., or about 37° C., to liquefy the cell stabilizing medium (or to maintain the cell stabilizing medium in a liquid state) before being mixed with a biological material (e.g., cells, tissues, organs, viral particles etc.) to form a mixture.

In certain embodiments, the cell stabilizing medium has a gelation time ranging from about 5 minutes to about 1 hour, from about 5 minutes to about 50 minutes, from about 5 minutes to about 40 minutes, from about 5 minutes to about 30 minutes, from about 8 minutes to about 30 minutes, from about 10 minutes to about 30 minutes, from about 15 minutes to about 25 minutes, from about 20 minutes to about 30 minutes, or from about 10 minutes to about 20 minutes. As used herein, the term "gelation time" refers to the time required for the present cell stabilizing medium to convert from its fluid phase into its gel phase.

In certain embodiments, the cell stabilizing medium (the gel phase of the cell stabilizing medium) has a bloom value ranging from about 125 to about 225, from about 175 to about 225, from about 190 to about 225, from about 175 to about 325, from about 190 to about 325, from about 225 to about 325, at least or equal to about 175, at least or equal to about 190, at least or equal to about 225, about 190, or about 200.

Other Components

In certain embodiments, the cell stabilizing medium further comprises a saccharide, an amino acid, a cytokine, a lipid, a growth factor, an antibiotic (e.g., penicillin, streptomycin, etc.), an antimycotic, a steroid hormone, a protein hormone, serum, amino acid analogues, amino acid derivatives, and divalent cation chelators, such as ethylenediaminetetraacetic acid (EDTA) or salts thereof, proteins, salts, formamide, methoxylated compounds, and/or polymers (e.g., polyvinyl pyrrolidone and polyvinyl alcohol), or a combination thereof. In certain embodiments, the cell stabilizing medium further comprises glycine, glycerol, sucrose, glucose, or combinations thereof.

In certain embodiments, the cell stabilizing medium comprises from about 300 mg/L to about 8,000 mg/L, from about 500 mg/L to about 7,000 mg/L, from about 1000 mg/L to about 6000 mg/L, from about 1000 mg/L to about 4500 mg/L, from about 500 mg/L to about 2300 mg/L, about 1,000 mg/L, about 4,500 mg/L, about 500 mg/L, or about 2,300 mg/L, of glucose.

Saccharides

Saccharides include oligosaccharides such as monosaccharides and disaccharides, polysaccharides, and the like. Saccharides include sugars.

Non-limiting examples of saccharides include sucrose, sorbitol, glucose, fructose, galactose, trehalose, mannose, raffinose, stachyose, dextran, xylose, arabinose, mannitol, xylitol, myo-inositol, lactose, maltose, cellobiose, lactitol, maltitol, methyl cellulose, carboxymethyl cellulose, glycogen, amylose, amylopectin, inulin, sodium alginate, ethyl cellulose, hydroxyethyl cellulose, xanthan gum, glucosamine, galactosamine, and combinations thereof. U.S. Pat. Nos. 6,673,607 and 7,094,601.

Amino Acids

The present cell stabilizing medium may or may not comprise one or more amino acids.

Amino acids include optical isomers, namely both D-isomers and L-isomers. Amino acids include alpha-amino acids, as well as beta-amino acids, gamma-amino acids, delta-amino acids, and unnatural amino acids. Non-limiting examples of amino acids include alanine, valine, leucine, isoleucine, proline, phenylalanine, tryptophan, methionine, glycine, serine, threonine, cysteine, glutamine, asparagine, tyrosine, lysine, arginine, aspartic acid, glutamic acid, and combinations thereof. Cryobiology, 41(4):257-279 (2000).

Amino acid derivatives may also be used in the present compositions and methods. Non-limiting examples of amino acid derivatives include amino acid salts and amino acid solvates. Non-limiting examples of the amino acid salts include alkaline metal salts or alkaline earth metal salts such as sodium salts, potassium salts, and calcium salts; halogen acid salts such as hydrofluoric acid salts, hydrochloric acid salts, hydrobromic acid salts, and hydroiodic acid salts; inorganic acid salts such as nitrate salts, perchlorate salts, sulfate salts, and phosphate salts; and organic acid salts such as fumarate salts, succinate salts, citrate salts, oxalate salts, maleate salts, acetate salts, lactate salts, and ascorbate salts. Non-limiting examples of the amino acid solvates include hydrates, alcoholates (for example, methanolates, ethanolates), and etherates (for example, diethyl etherates).

In certain embodiments, the amino acid concentration in the present cell stabilizing medium is 0.01-10.0% by weight, or 0.1-1.0% by weight.

Vitamins

In another embodiment, the cell stabilizing medium further comprises one or more vitamins Non-limiting examples of vitamins include D-calcium pantothenate, choline chloride, folic acid, niacinamide, pyridoxine HCl, thiamine HCl, and riboflavin.

Salts

In certain embodiments, the present cell stabilizing medium further comprises one or more salts, including inorganic salts, and/or organic salts. Non-limiting examples of inorganic salts include, potassium chloride, sodium bicarbonate, sodium chloride, and sodium phosphate monobasic, potassium phosphate monobasic, potassium phosphate dibasic, sodium bicarbonate, calcium chloride, magnesium chloride, potassium bicarbonate, potassium monophosphate, and combinations thereof.

In certain embodiments, the cell stabilizing medium or the composition does not comprise serum. In certain embodiments, the cell stabilizing medium or the composition does not comprise any raw materials of direct human or animal origin, or materials that have been produced using materials of human or animal origin.

The cell stabilizing medium or the composition may comprise other optional components, including, but not limited to, peptides, other proteins, sugar alcohols, amino saccharides, glycoproteins, and alcohols, pH controlling agents, moisturizing agents, preservatives, viscosity controlling agents, or combinations thereof. U.S. Pat. No. 9,055,739.

Thawing

In certain embodiments, the biological material (cells, tissues, organs) is thawed (or has been thawed) from cryopreservation (a cryopreserved state), before or during mixing with the present cell stabilizing medium.

The appropriate storage conditions for preserving a biological material may comprise any such conditions that maintain the biological material viable. Such conditions can include a cryopreservation temperature of at or below about 0° C., at or below about −20° C., at or below about −50° C., at or below about −60° C., at or below about −70° C., at or below about −80° C., at or below about −90° C., at or below about −100° C., at or below about −110° C., at or below about −120° C., at or below about −135° C., at or below about −196° C., or in liquid nitrogen. For hypothermic preservation, the temperature can be between 8° C. and 0° C. In the case of lyophilized samples, the temperature may be any temperature above 0° C. (e.g., room temperature, an ambient temperature, etc.) or below 0° C., as long as, the material is kept away from humidity.

The biological material can remain in a preserved state (e.g., a cryopreserved state) for periods of days, weeks, months or years, until the biological material is required. When required, the cryopreserved biological material is retrieved and thawed.

In certain embodiments, the biological material in the cryopreservation composition is thawed in a water bath (e.g., by placing the cryotube or cryovial in a water bath), at a temperature at or below about 42° C., from about 10° C. to about 40° C., from about 20° C. to about 37° C., room temperature, or about 37° C.

In one embodiment, the biological material in the cryopreservation composition is thawed in a water bath at about 37° C. Optionally, it would be then moved to a lower temperature such as 4° C. or on ice.

In certain embodiments, a "step up" thawing process having a step up heating rate (or a temperature ramp-up heating rate) is used. For example, the cryovial may be placed in sequential storage environments with increasing temperatures before being transferred to a temperature that is around body temperature, for example a water bath having a temperature of around 37° C., or any other suitable temperature.

In certain embodiments, the cryopreserved biological material in the cryopreservation composition is thawed at a warming rate ranging from about 5° C./min to about 80° C./min, from about 10° C./min to about 70° C./min, from about 10° C./min to about 60° C./min, from about 10° C./min to about 50° C./min, from about 10° C./min to about 40° C./min, from about 10° C./min to about 30° C./min, about 10° C./min to about 20° C./min, from about 20° C./min to about 40° C./min, greater than about 20° C./min, greater than about 25° C./min, greater than about 30° C./min, greater than about 35° C./min, greater than about 40° C./min, or about 30° C./min.

In certain embodiments, after thawing, before or after being treated with the present cell stabilizing medium, the biological material is washed, suspended in the appropriate media and treated as needed for use in research or clinical applications.

In certain embodiments, after thawing and after being treated with the present cell stabilizing medium, the cells are transferred to a culture dish for re-culturing. The cells may be cultured under appropriate conditions for a period of about 30 minutes, about 1 hour, about 6 hours, about 12 hours, about 24 hours, about 48 hours, about 72 hours, about 86 hours, about 110 hours, about 1 week, about 2 weeks, or more than 3 weeks prior to research or clinical applications. U.S. Patent Publication No. 20170196221.

In certain embodiments, resuscitation of adherent cells or semi-adherent cells are re-cultured immediately upon thawing and after treatment with the present cell stabilizing medium.

In certain embodiments, after thawing and after treatment with the present cell stabilizing medium, the biological material is used in vivo without an intervening culturing step.

In certain embodiments, after thawing and after treatment with the present cell stabilizing medium, the cells may be re-suspended in a fluid or other medium suitable for the intended use. For example, the cells can be re-suspended in any osmotically supportive solution. In certain embodiments, the cells can be re-suspended in a physiologically compatible buffer, such as the buffer solutions described herein. Preferably, any physiologically compatible material providing a composition for convenient delivery in vivo can be used to re-suspend the cells.

Viability of Cells

The present compositions and methods maintain cell viability.

As used herein, the term "viability" refers to the percentage of viable biological material (such as cells, e.g., based on the presence of DNA and/or an intact cell membrane system, or viable viruses). In certain embodiments, viable biological material refers to a biological material comprising some viable cells or fractions of cells that are metabolically active or would become metabolically active after their release from the preservation state.

In certain embodiments, the viability of the biological material (e.g., cells or viruses) is at least about 50%, at least about 55%, at least about 60%, at least about 65%, at least about 70%, at least about 75%, at least about 80%, at least about 85%, at least about 90%, or at least about 95%.

In certain embodiments, the present compositions and methods ensure that the cells display a limited amount of, or minimal, necrosis and apoptosis. In certain embodiments, necrosis and/or apoptosis is observed in less than about 25%, less than about 20%, less than about 15%, less than about 10%, less than about 5%, or less than about 1% of the cells.

The viability can be measured by any methods known in the art. In certain embodiments, the viability is measured using a Trypan blue internalization test or by measuring propidium iodide uptake. In certain embodiments, the viability is measured by assaying the ability of cells to attach efficiently (e.g., the attachment assays). In certain embodiments, proliferation assays can be used to determine if the attached cells can proliferate as expected after cryopreservation. Attachment and proliferation efficiency can be compared to control cells which have not undergone cryopreservation.

There are various tests known in the art to determine the viability and function of the cells. In certain embodiments, these tests are dependent on the cell type and the desired use of the cell.

For stem cells or progenitor cells, the methods described herein may further ensure that the cells maintain their pluripotency. This can be established by the determination of expression of lineage-specific markers. For instance, functional characterization of the mesenchymal stem cells may include induction of adipogenic, osteogenic and chondrogenic differentiation in vitro using commercially available differentiation kits and RT-PCR to detect lineage specific expression of mRNA, indicative for adipogenic, osteogenic and chondrogenic differentiation potential. Similarly, the quality of the undifferentiated stem cells can be tested by isolation of mRNA and testing on cell-specific markers. In particular embodiments, the ability to differentiate into a cell of the specified lineage is maintained, i.e., does not significantly differ from unprocessed cells. The pluripotency of the embryonic stem (ES) cells can be tested using art known methods, including, for example, Oct4-GFP expression, elevated alkaline phosphatase expression, and SSEA-1 surface glycoprotein expression. Several in vitro methods can be applied to assess stem cell recovery after experimental treatment. These assessments may include, but are not limited to, membrane integrity, metabolic and other functional assays and/or colony growth in culture, and fluorescent assays, such as SYTO/EB. In certain embodiments, differentiation tests, immunophenotype characterization, and/or an inspection of the morphology may be used to assay stem cells and/or progenitor cells.

For zygotes, cleavage rates can be determined and compared to control groups to determine if there has been any cellular damage. The viability of oocytes can be determined by examination of the morphological characteristics of the cells following cryopreservation. Morphologically viable oocytes exhibit intact zona pellucida and plasma membrane and refractive cytoplasm, while non-viable oocytes appear degenerated when visualized under a light microscope. The ultimate criterion for oocyte viability and function is their capability to be fertilized by healthy sperm in vitro and in vivo, followed by cleavage, blastocyst, and/or hatching or development of the fetus. U.S. Pat. No. 9,538,745.

In certain embodiments, the present preservation compositions and methods, as well as the biological material, can be used for research and/or clinical application (e.g., cell-based therapies, transplantation, regenerative medicine, diagnostics and genetic testing, cell/tissue banking for surveillance, toxicity testing and for in vitro fertilization).

Biological Materials

The term "biological material" denotes cells, cell aggregates, tissue, organs, biological fluids, viral particles, and any other membranous entity such as liposomes (natural or synthetic).

Any type of cells or tissues may be treated with the present compositions (e.g., the cell stabilizing medium) and methods.

In certain embodiments, the cells are mammalian cells, including, but not limited to, human cells, murine cells, porcine cells, canine cells, equine cells and bovine cells. The cells may be from a mammal that is of an endangered or threatened species. The cells may be from a human or non-human mammal, for example Cercopithecoidea family, Hominoidea superfamily, *Canis familiaris, Felis catus, Cricetidae* spp., *Equus* spp. (e.g., *Equus caballus, Equus assinus*), Equidae family, *Bos taurus, Bos indicus*, Bovidae family, Camelidae family, *Bubalus bubalis, Capra aegagrus hircus,* Cervidae family, Cervinae family, *Ovis aries, Ovis canadensis, Capra hircus, Sus scrofa domestica, Mesocricetus* spp., *Mustela vison, Cavia porcellus, Meriones unguiculatus, Chinchilla laniger, Rattus norvegicus, Rattus* spp., *Mus musculus,* Leporidae family, *Oryctolagus cuniculus, Kobus* spp., *Gallus* spp., *Meleagria gallopavo,* Anatidae spp., *Mustela putorius, Columba domestica, Columba livia, Numida meleagris, Ornithorhynchus anatinus, Pavo cristatus, Bison* spp., *Struthio* spp., *Lama glama, Rhea* spp., *Dromiceius* spp., *Lama pacos, Rangifer tarandus, Bos grunniens, Camelus bactrianus, Camelus dromedarius*), and any endangered or threatened species.

The present compositions and methods may be used to treat microorganisms, bacteria, non-mammalian animal cells (e.g., insect cells, avian cells, fish cells, etc.), or plant cells.

Non-limiting examples of the cell include stem cells, progenitor cells, embryos, sperm, oocytes, gametocytes, and zygotes.

The cells may be tumor cells or non-tumor cells. In one embodiment, the cells are fibroblasts.

Biological materials may comprise, without limitation, any of the following: fibroblasts, stem cells, progenitor cells, whole blood or fractions thereof, red blood cells, white blood cells, umbilical cord blood or fractions thereof, umbilical cord blood cells, bone marrow, oocytes, sperm, ova, embryos, cartilage, ovary, heart, skin, kidney, liver, lung. In addition, such biological material may comprise cellular organisms, which may be eukaryotes or prokaryotes, including bacteria, and yeast, etc. Additionally, biological material may also comprise whole multi-cellular organisms that are capable of surviving cryopreservation such as nematodes. Fractions of blood may comprise any fraction of blood comprising blood cells (white and/or red), plasma and/or solutes and/or sub-cellular components (e.g. fractions of cells, such as platelets, components of degraded cells, etc.), proteins, lipids, antibodies, etc.

The present compositions and methods may be used to treat any types of cells, including but not limited to, cellular materials derived from tissues and organs, including, but not limited to, pancreatic islet cells, chondrocytes, cells of neural origin, cells of hepatic origin, cells of opthalmolic origin, cells of orthopedic origin, cells from connective tissues, and cells of reproductive origin, and cells of cardiac and cardiovascular origin.

Stem cells include adult stem cells, embryonic stem cells, induced pluripotent stem cells (iPSCs), peripheral blood stem cells, umbilical cord blood stem cells, mesenchymal stem cells, stem cells derived from tissues and organs or other sources, including fetal and/or embryonic sources, as well as mixtures of stem cells with other cells and from different sources. Adult stem cells include bone marrow stem cells, hematopoietic stem cells, skin stem cells, ocular stem cells, neural stem cells, cardiac stem cells, etc.

In certain embodiments, the stem cells of endodermal origin are pulmonary epithelial stem cells, gastrointestinal tract stem cells, pancreatic stem cells or hepatic oval cells and/or progenitor cells thereof. In particular embodiments, the cells of urogenital origin are either categorized as mammary and prostatic gland stem cells or ovarian and testicular stem cells and/or progenitor cells thereof. In particular embodiments, the cells of mesodermal origin are bone marrow cells, hematopoietic stem cells, stromal stem cells or cardiac stem cells and/or progenitor cells thereof. In particular embodiments, the cells of ectodermal origin are neural stem cells, skin stem cells or ocular stem cells and/or progenitor cells thereof.

Cell types that may be treated using the compositions (e.g., the cell stabilizing medium) and methods of the present disclosure include, for example, differentiated cells, such as fibroblasts, epithelial cells, cardiomyocytes, hepatocytes, neural cells, epidermal cells, keratinocytes, hematopoietic cells, melanocytes, chondrocytes, B-cells, T-cells, erythrocytes, macrophages, monocytes, or muscle cells; and undifferentiated cells, such as embryonic, mesenchymal, or adult stem cells. The cells can be haploid, diploid, or tetraploid. Other cells include cells from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

In further particular embodiments, the cells are obtained from adult brain, bone marrow, blood vessels, skeletal muscle, skin, teeth, heart, gut, liver, or other adult tissues. In particular embodiments, the cells are selected from the group consisting of endodermal, urogenital, mesodermal or ectodermal origin.

Tissues include cornea, cartilage, bone, skin, heart valves, Islets of Langerhans, embryos from humans, animals, fish, shellfish and plants, and ovarian tissues from humans and animals. The present compositions and methods may also treat engineered tissues and tissue constructs.

In certain embodiments, the present compositions and methods can be used to treat oocytes or sperm in assisted reproductive technology, or for patients undergoing chemotherapy or radiation therapy. The method can also be used for the treatment of stem cells, which can then be used as the basis of stem cell-based therapies, cell transplantation, tissue engineering, and regenerative medicine. The method can also be used to treat oocytes or sperm from an animal that is rare or at risk of becoming extinct for future use in assisted reproductive technologies for the preservation of the species. The method can further be used for animal husbandry purposes (e.g., the breeding and raising of animals), for example, for treating embryonic stem cells, gametocytes, oocytes, or sperm from animals such as cows, pigs, and sheep.

The biological material may be useful for the treatment of a variety of diseases. For example, in several embodiments, ocular cells are used to treat ocular diseases including, but not limited to age related macular degeneration (wet or dry), diabetic macular edema, idiopathic choroidal neovascularization, or high myopia macular degeneration. In some ocular embodiments, RPE cells are used. In several embodiments, cardiac stem cells are used to treat cardiovascular disorders such as myocardial infarction, ischemic cardiac tissue damage, congestive heart failure, aneurysm, atherosclerosis-induced events, cerebrovascular accident (stroke), and coronary artery disease. In several embodiments, liver stem cells are used to treat liver disease such as hepatitis, cirrhosis, cancer, and the like. Diseases in other tissues, such as the kidney, lung, pancreas, intestine, bone and/or cartilage, and neural tissues, among others, may be treated with the methods and devices disclosed herein. In some embodiments, harvested bone marrow stem cells may be used to repopulate hematopoietic cells that are reduced due to leukemias, cancers, or therapies that reduce blood cell counts.

The present compositions and methods are also useful in various methods of treatment. Cellular therapy, or cell therapy, can generally encompass transplantation of human or animal cells to replace or repair damaged tissue and/or cells. Cell therapy has been used to rebuild damaged cartilage in joints, repair spinal cord injuries, strengthen a weakened immune system, treat autoimmune diseases, and help patients with neurological disorders such as Alzheimer's disease, Parkinson's disease, and epilepsy. Further uses have included treatment of a wide range of chronic conditions such as arteriosclerosis, congenital defects, and sexual dysfunction.

Cell therapy typically involves the injection of either whole cells or cell extracts that are xenogenic, allogenic (from another human donor), or autologous (wherein the cells are extracted from and transplanted back into the same patient).

Viruses or viral particles can be any viruses. In certain embodiments, the viruses or viral particles comprises adenoviruses, adeno-associated viruses, retroviruses, herpes viruses and the like. In certain embodiments, the viruses or viral particles are those which may be used in gene therapy.

Kits

The present disclosure also provides for a kit comprising the present cell stabilizing medium (in solid or liquid form as described herein) or the present composition. Such kits may include one or more containers comprising the cell stabilizing medium or present composition. In one embodiment, the kit comprises the cell stabilizing medium or present composition (which may or may not comprise a biological material). In one embodiment, the kit comprises the biological material for treating with the present cell stabilizing medium.

In some embodiments, the kit can comprise instructions for use in any of the methods described herein. In one embodiment, the kit comprises instructions for treating a biological material using the cell stabilizing medium and method. The kit may further comprise a description of selecting a subject suitable for treatment based on identifying whether the subject is in need of the treatment. In some embodiments, the instructions comprise a description of administering the biological material treated with the present cell stabilizing medium to a subject who is in need of the treatment. In certain embodiments, instructions supplied in the kits are written instructions on a label or package insert. The label or package insert may also indicate clinical and/or research applications of the biological material.

Parts of a kit may be used simultaneously or chronologically staggered, i.e., at different points in time and with equal or different time intervals for any component of a kit. Time intervals can be selected to obtain the desired effect.

The kits provided herein are in suitable packaging. Suitable packaging includes, but is not limited to, a vial (e.g., a cryovial), a bottle, an ampoule, a tube (e.g., a cryotube), a bag, a flask, a jar, flexible packaging, and the like. Also contemplated are packages for use in combination with a specific device, such as a freezing container, a cryovial and/or a cryotube.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

The following are examples of the present invention and are not to be construed as limiting.

Example 1

Experiment No. 1

Gelatin was obtained from Gelita (gelatin was prepared from bovine hides; Batch No. L600217). A cell stabilizing medium containing 15.7 wt % gelatin was prepared by dissolving gelatin in DMEM.

FE002-SK2 cells, which are fetal skin fibroblast cells, in a cryopreservation composition comprising glycerol were thawed from cryopreservation. This cell suspension was then mixed with the cell stabilizing medium to form a mixture.

As a control sample, cells in a cryopreservation composition comprising glycerol were thawed from cryopreservation, and then the cell suspension was mixed with DMEM to form a mixture.

The volume ratio of the cell stabilizing medium (or DMEM for the control samples) to the cell suspension is 12.5. The cells (in the cell suspension) and the cell stabilizing medium (or DMEM for the control samples) were mixed by aspiration using 1000 μL PIPETMAN® and tips.

The mixture was incubated at 30° C. or 37° C. for 0 hour (Time 0, no incubation), 2 hours, or 4 hours. Samples for each condition were duplicated. The total number of the cells, the number of the live cells and the number of the dead cells were assayed by using ADAM-MC Automatic Cell Counter (Digital Bio). Viability of the cells was calculated by the following formula: [(live cell number)/(total cell number)]×100%.

As shown in Table 1, cells in the cell stabilizing medium comprising gelatin maintained their viability after being incubated at 30° C. or 37° C. for 2 hours or 4 hours. In other words, after being incubated at 30° C. or 37° C. for 2 hours or 4 hours, the viability of the cells was similar to their viability at Time 0. In contrast, the viability of the cells mixed with DMEM reduced about 48% (2 hours) or 56% (4 hours) after being incubated at 30° C. or 37° C. for 2 hours or 4 hours. This experiment confirms the protective effect of the cell stabilizing medium containing gelatin.

TABLE 1

| Incubation time | Incubation Temp. ° C. | Cell suspension mixed with cell stabilizing medium containing gelatin | | Cell suspension mixed with DMEM | |
|---|---|---|---|---|---|
| | | Cell Viability | Average Viability | Cell Viability | Average Viability |
| 0 | 37 | 80% 78% | 79% | 75% 79% | 77% |
| 2 hours | 30 | 81% 75% | 78% | 29% 39% | 34% |
| | 37 | 84% 79% | 82% | 40% 25% | 33% |

TABLE 1-continued

| Incubation time | Incubation Temp. ° C. | Cell suspension mixed with cell stabilizing medium containing gelatin | | Cell suspension mixed with DMEM | |
|---|---|---|---|---|---|
| | | Cell Viability | Average Viability | Cell Viability | Average Viability |
| 4 hours | 30 | 78% 73% | 75% | 39% 49% | 40% |
| | 37 | 75% 76% | 76% | 25% 45% | 40% |

Experiment No. 2

Gelatin was obtained from GELITA (Lot. L600217). A cell stabilizing medium containing 15.7 wt % gelatin was prepared by dissolving gelatin in water.

Cells in a cryopreservation composition comprising glycerol were thawed from cryopreservation. This cell suspension was then mixed with the cell stabilizing medium to form a mixture. The volume ratio of the cell stabilizing medium to the cell suspension is 12.5. The cells (in the cell suspension) and the cell stabilizing medium were mixed by aspiration using 1000 μL PIPETMAN® and tips.

The mixture was incubated at 37° C. for 0 hour (Time 0, no incubation), 1 hour, 2 hours, 4 hours, 8 hours, or 24 hours. Samples for each condition were duplicated. The total number of the cells, the number of the live cells and the number of the dead cells were assayed by using ADAM-MC Automatic Cell Counter (Digital Bio). Viability of the cells was calculated as described in herein.

As shown in Table 2, cells in the cell stabilizing medium comprising gelatin maintained their viability after being incubated at 37° C. up to 4 hours (for 1 hour, 2 hours or 4 hours). In other words, after being incubated at 37° C. for up to 4 hours, the viability of the cells was similar to their viability at Time 0. After 8 hours of incubation at 37° C., the cell viability can still be maintained to be above 70%. This experiment confirms the protective effect of the cell stabilizing medium containing gelatin.

TABLE 2

| 37° C. Incubation | Cell Viability | Average Viability |
|---|---|---|
| 0 hour | 78% 78% | 78% |
| 1 hour | 80% 80% | 80% |
| 2 hour | 77% 79% | 78% |
| 4 hour | 78% 81% | 79.5% |
| 8 hour | 70% 76% | 73% |
| 24 hour | 41% 36% | 38.5% |

Experiment No. 3

Gelatin was obtained from GELITA (Lot. L600217). A cell stabilizing medium containing 15.7 wt % gelatin was prepared by dissolving gelatin in water.

Cells in a cryopreservation composition comprising DMSO were thawed from cryopreservation. This cell suspension was then mixed with the cell stabilizing medium to form a mixture. As a control sample, cells in a cryopreservation composition comprising DMSO were thawed from cryopreservation, and then the cell suspension was mixed with DMEM or 10% FBS/DMEM to form a mixture.

The volume ratio of the cell stabilizing medium (or DMEM for the control samples) to the cell suspension is 10. The cells (in the cell suspension) and the cell stabilizing medium (or DMEM, or 10% FBS/DMEM, for the control samples) were mixed by aspiration using 1000 μL PIPETMAN® and tips.

The mixture was incubated at 25° C. for 0 hour (Time 0, no incubation), 2 hours, 4 hours, or 8 hours. Samples for each condition were duplicated. The total number of the cells, the number of the live cells and the number of the dead cells were assayed by using ADAM-MC Automatic Cell Counter (Digital Bio). Viability of the cells was calculated.

As shown in Table 3, cells in the cell stabilizing medium comprising gelatin maintained their viability after being incubated at 25° C. for 2 hours or 4 hours. In other words, after being incubated at 25° C. for 2 hours or 4 hours, the viability of the cells was similar to their viability at Time 0. After 8 hours of incubation at 25° C., the cell viability can still be maintained to be above 80%. In contrast, the viability of the cells mixed with DMEM reduced about 13% (2 hours), 21% (4 hours), or 32% (8 hours) after being incubated at 25° C. for up to 8 hours. Similarly, the viability of the cells mixed with 10% FBS/DMEM reduced about 19% (2 hours) or 34% (4 hours or 8 hours) after being incubated at 25° C. for up to 8 hours. This experiment confirms the protective effect of the cell stabilizing medium containing gelatin.

TABLE 3

| Incubation time | Cell suspension mixed with cell stabilizing medium containing gelatin | | Cell suspension mixed with DMEM | | Cell suspension mixed with 10% FBS/DMEM | |
|---|---|---|---|---|---|---|
| | Cell Viability | Average Viability | Cell Viability | Average Viability | Cell Viability | Average Viability |
| 0 | 93% 87% | 90% | 81% 86% | 83.5% | 84% 85% | 84.5% |
| 2 hrs | 87% 88% | 87.5% | 72% 74% | 73% | 68% 69% | 68.5% |
| 4 hrs | 86% 83% | 84.5% | 62% 70% | 66% | 58% 54% | 56% |
| 8 hrs | 82% 83% | 82.5% | 55% 58% | 56.5% | 55% 56% | 55.5% |

Experiment No. 4

Gelatin was obtained from Nippi (gelatin was prepared from bovine, swine and/or fish, etc. source; Lot No. S150806). A cell stabilizing medium containing 10 wt % gelatin was prepared by dissolving gelatin in water.

Cells in a cryopreservation composition comprising glycerol were thawed from cryopreservation. This cell suspension was then mixed with the cell stabilizing medium to form a mixture. The volume ratio of the cell stabilizing medium to the cell suspension is 12.5.

Differently from Experiment Nos. 1-3, in this experiment, the cells (in the cell suspension) and the cell stabilizing medium were mixed by aspiration using a syringe with a needle. In a clinical setting, an 18G needle connected to a syringe will be used to aspirate and mix cells and the cell stabilizing medium.

The mixture was incubated at 37° C. for 0 hour (Time 0, no incubation), 2 hours, 4 hours, 6 hours, 8 hours, or 24 hours. Samples for each condition were either triplicated or duplicated. The total number of the cells, the number of the live cells and the number of the dead cells were assayed by using ADAM-MC Automatic Cell Counter (Digital Bio). Viability of the cells was calculated as described in herein.

As shown in Table 4, cells in the cell stabilizing medium comprising gelatin maintained their viability after being incubated at 37° C. up to 6 hours (for 2 hours, 4 hours, or 6 hours). In other words, after being incubated at 37° C. for up to 4 hours, the viability of the cells was similar to their viability at Time 0. After 8 hours of incubation at 37° C., the cell viability slightly decreased. After 24 hours of incubation at 37° C., the cell viability decreased to about 30%. This experiment confirms the protective effect of the cell stabilizing medium containing gelatin.

TABLE 4

| Incubation Time | Cell viability | Average Cell viability (mean ± SD) |
|---|---|---|
| 0 hr | 80% 77% 77% | 78 ± 1.7% |
| 2 hr | 86% 84% 86% | 85.3 ± 1.2% |
| 4 hr | 86% 79% 81% | 82 ± 3.6% |
| 6 hr | 83% 80% 82% | 81.7 ± 1.5% |
| 8 hr | 80% 70% 67% | 72.3 ± 6.8% |
| 24 hr | 38% 20% | 29 ± 12.7% |

As used herein, "SD" stands for standard deviation.

Experiment No. 5

Gelatin was obtained from Nippi (Lot. S150806). A cell stabilizing medium containing 10 wt % gelatin was prepared by dissolving gelatin in water.

Cells in a cryopreservation composition comprising glycerol were thawed from cryopreservation. This cell suspension was then mixed with the cell stabilizing medium to form a mixture. The volume ratio of the cell stabilizing medium to the cell suspension is 12.5.

The cells (in the cell suspension) and the cell stabilizing medium were mixed by aspiration using a syringe with a needle. In a clinical setting, an 18G needle connected to a syringe will be used to aspirate and mix cells and the cell stabilizing medium.

The mixture was incubated at 25° C. or 30° C. for 0 hour (Time 0, no incubation), 2 hours, 4 hours, 6 hours, 8 hours, or 24 hours, or 72 hours. Samples for each condition were either triplicated or duplicated. The total number of the cells, the number of the live cells and the number of the dead cells were assayed by using ADAM-MC Automatic Cell Counter (Digital Bio). Viability of the cells was calculated as described in herein.

As shown in Table 5, cells in the cell stabilizing medium comprising gelatin maintained their viability after being incubated at 25° C. for up to 24 hours (for 2 hours, 4 hours, 6 hours, 8 hours, or 24 hours). In other words, after being incubated at 25° C. for up to 24 hours, the viability of the cells was similar to their viability at Time 0. Cells in the cell stabilizing medium comprising gelatin maintained their viability after being incubated at 30° C. for up to 8 hours (for 2 hours, 4 hours, 6 hours, or 8 hours). In other words, after being incubated at 30° C. for up to 8 hours, the viability of the cells was similar to their viability at Time 0. After 24 hours of incubation at 30° C., the cell viability can still be maintained to be above 70%.

TABLE 5

| | 25° C. | | 30° C. | |
| --- | --- | --- | --- | --- |
| Incubation Time | Cell viability | Average Cell viability (mean ± SD) | Cell viability | Average Cell viability (mean ± SD) |
| 0 hr | 75% 74% | 74.5 ± 0.7% | 75% 74% | 74.5 ± 0.7% |
| 2 hr | 81% 79% 83% | 81 ± 2% | 80% 84% 83% | 82.3 ± 2.1% |
| 4 hr | 83% 82% 85% | 83.3 ± 1.5% | 81% 86% 86% | 84.3 ± 2.9% |
| 6 hr | 86% 85% 81% | 84 ± 2.6% | 80% 86% 83% | 83 ± 3% |
| 8 hr | 86% 85% 87% | 86 ± 1% | 80% 85% 82% | 82.3 ± 2.5% |
| 24 hr | 86% 85% 81% | 84 ± 2.6% | 80% 77% 75% | 77.3 ± 2.5% |
| 72 hr | 46% 57% | 51.5 ± 7.8% | 14% 9% | 11.5 ± 3.5% |

Experiment No. 6

Gelatin was obtained from Nippi (Lot. S150806). A cell stabilizing medium containing 5 wt % gelatin was prepared by dissolving gelatin in water.

Cells in a cryopreservation composition comprising glycerol were thawed from cryopreservation. This cell suspension was then mixed with the cell stabilizing medium to form a mixture.

As a control sample, cells in a cryopreservation composition comprising glycerol were thawed from cryopreservation, and then the cell suspension was mixed with DMEM to form a mixture.

The volume ratio of the cell stabilizing medium (or DMEM for the control samples) to the cell suspension is 12.5. The cells (in the cell suspension) and the cell stabilizing medium (or DMEM for the control samples) were mixed by aspiration using 1000 μL PIPETMAN® and tips.

The mixture was incubated at 37° C. for 0 hour (Time 0, no incubation), or 2 hours. The total number of the cells, the number of the live cells and the number of the dead cells were assayed by using ADAM-MC Automatic Cell Counter (Digital Bio). Viability of the cells was calculated.

As shown in Table 6, after being incubated at 37° C. for 2 hours, the viability of the cells mixed with the cell stabilizing medium containing gelatin was higher than the viability of the cells mixed with DMEM.

TABLE 6

| | Cell suspension mixed with cell stabilizing medium containing gelatin | | Cell suspension mixed DMEM | |
| --- | --- | --- | --- | --- |
| Incubation Time | Cell Viability | Average Viability | Cell Viability | Average Viability |
| 0 | 86% — | 86% | 72% 63% | 67.5% |
| 2 hrs | 65% 69% | 67% | 43% — | 43% |

Experiment No. 7

Gelatin was obtained from Nippi (Lot. S150806). A cell stabilizing medium containing 6 wt % gelatin was prepared by dissolving gelatin in water.

Cells in a cryopreservation composition comprising glycerol were thawed from cryopreservation. This cell suspension was then mixed with the cell stabilizing medium to form a mixture.

As a control sample, cells in a cryopreservation composition comprising glycerol were thawed from cryopreservation, and then the cell suspension was mixed with DMEM to form a mixture.

The volume ratio of the cell stabilizing medium (or DMEM for the control samples) to the cell suspension is 12.5. The cells (in the cell suspension) and the cell stabilizing medium (or DMEM for the control samples) were mixed by aspiration using 1000 μL PIPETMAN® and tips.

The mixture was incubated at 37° C. for 0 hour (Time 0, no incubation), or 2 hours. The total number of the cells, the number of the live cells and the number of the dead cells were assayed by using ADAM-MC Automatic Cell Counter (Digital Bio). Viability of the cells was calculated.

As shown in Table 7, after being incubated at 37° C. for 2 hours, the viability of the cells mixed with the cell stabilizing medium containing gelatin was higher than the viability of the cells mixed with DMEM.

TABLE 7

| | Cell suspension mixed with cell stabilizing medium containing gelatin | | Cell suspension mixed DMEM | |
| --- | --- | --- | --- | --- |
| Incubation Time | Cell Viability | Average Viability | Cell Viability | Average Viability |
| 0 | 86% — | 86% | 72% 63% | 67.5% |
| 2 hrs | 65% 69% | 67% | 43% — | 43% |

Experiment No. 8

Gelatin was obtained from Nippi (Lot. S150806). A cell stabilizing medium containing 7.5 wt % gelatin was prepared by dissolving gelatin in water.

Cells in a cryopreservation composition comprising glycerol were thawed from cryopreservation. This cell suspension was then mixed with the cell stabilizing medium to form a mixture.

As a control sample, cells in a cryopreservation composition comprising glycerol were thawed from cryopreservation, and then the cell suspension was mixed with DMEM to form a mixture.

The volume ratio of the cell stabilizing medium (or DMEM for the control samples) to the cell suspension is 12.5. The cells (in the cell suspension) and the cell stabilizing medium (or DMEM for the control samples) were mixed by aspiration using 1000 μL PIPETMAN® and tips.

The mixture was incubated at 37° C. for 0 hour (Time 0, no incubation), or 2 hours. The total number of the cells, the number of the live cells and the number of the dead cells were assayed by using ADAM-MC Automatic Cell Counter (Digital Bio). Viability of the cells was calculated.

As shown in Table 8, after being incubated at 37° C. for 2 hours, the viability of the cells mixed with the cell stabilizing medium containing gelatin was higher than the viability of the cells mixed with DMEM.

TABLE 8

| Incubation Time | Cell suspension mixed with cell stabilizing medium containing gelatin | | Cell suspension mixed DMEM | |
|---|---|---|---|---|
| | Cell Viability | Average Viability | Cell Viability | Average Viability |
| 0 | 86% | 86% | 72% | 67.5% |
| | — | | 63% | |
| 2 hrs | 70% | 69% | 43% | 43% |
| | 68% | | — | |

Experiment No. 9

Gelatin was obtained from GELITA (Lot. L600217). A cell stabilizing medium containing 15.7 wt % gelatin was prepared by dissolving gelatin in water.

Cells in a cryopreservation composition comprising glycerol were thawed from cryopreservation. This cell suspension was then mixed with the cell stabilizing medium to form a mixture.

The volume ratio of the cell stabilizing medium to the cell suspension is 6.25. The cells (in the cell suspension) and the cell stabilizing medium were mixed by aspiration using 1000 μL PIPETMAN® and tips.

The mixture was incubated at 27° C. or 37° C. for 0 hour (Time 0, no incubation), 2 hours, or 4 hours. Samples for each condition were duplicated. The total number of the cells, the number of the live cells and the number of the dead cells were assayed by using ADAM-MC Automatic Cell Counter (Digital Bio). Viability of the cells was calculated.

As shown in Table 9, cells in the cell stabilizing medium comprising gelatin maintained their viability after being incubated at 27° C. or 37° C. for 2 hours or 4 hours. In other words, after being incubated at 27° C. or 37° C. for 2 hours or 4 hours, the viability of the cells was similar to their viability at Time 0.

TABLE 9

| Incubation time | Incubation Temp. (° C.) | Cell suspension mixed with cell stabilizing medium containing gelatin | |
|---|---|---|---|
| | | Cell Viability | Average Viability |
| 0 | 37 | 67% | 66% |
| | | 65% | |
| 2 hours | 27 | 74% | 72.5% |
| | | 71% | |
| | 37 | 66% | 68% |
| | | 70% | |

TABLE 9-continued

| Incubation time | Incubation Temp. (° C.) | Cell suspension mixed with cell stabilizing medium containing gelatin | |
|---|---|---|---|
| | | Cell Viability | Average Viability |
| 4 hours | 27 | 73% | 73% |
| | | 73% | |
| | 37 | 66% | 65.5% |
| | | 65% | |

Experiment No. 10

Gelatin was obtained from GELITA (Lot. L600217). A cell stabilizing medium containing 15.7 wt % gelatin was prepared by dissolving gelatin in water.

Cells in a cryopreservation composition comprising glycerol were thawed from cryopreservation. This cell suspension was then mixed with the cell stabilizing medium to form a mixture. The volume ratio of the cell stabilizing medium to the cell suspension is 12.5.

The cells (in the cell suspension) and the cell stabilizing medium were mixed by aspiration using a syringe with a needle. In a clinical setting, an 18G needle connected to a syringe will be used to aspirate and mix cells and the cell stabilizing medium.

The mixture was incubated at 23° C., 27° C., or 30° C. for 0 hour (Time 0, no incubation), 1 hour, or 2 hours. Samples for each condition were duplicated. The total number of the cells, the number of the live cells and the number of the dead cells were assayed by using ADAM-MC Automatic Cell Counter (Digital Bio). Viability of the cells was calculated as described in herein (Table 10).

TABLE 10

| Incubation time | Incubation Temp. (° C.) | Cell Viability | Average Viability |
|---|---|---|---|
| 1 hr | 23 | 49% | 54% |
| | | 59% | |
| | 27 | 71% | 68% |
| | | 65% | |
| | 30 | 74% | 75.5% |
| | | 77% | |
| 2 hrs | 23 | 44% | 37% |
| | | 30% | |
| | 27 | 51% | 51% |
| | | 51% | |
| | 30 | 74% | 74.5% |
| | | 75% | |

Example 2 Effects of Gelatin Concentration and Temperature on Cell Viabilities

The experimental conditions are shown in Table 11.

TABLE 11

| Temperature | 25° C., or 37° C. |
|---|---|
| Gelatin concentration | 1 wt %, 3 wt %, 17 wt % |
| Volume ratio of cell stabilizing medium to cell suspension | 5, or 12.5 |
| Incubation time | 0, 2, 4, 8 hrs |

Cell stabilizing media containing 1 wt %, 3 wt %, or 17 wt % gelatin was prepared. The cell stabilizing medium was incubated in a 37° C. water bath to ensure conversion to fluid phase before being mixed with the cells.

Cells were expanded, harvested and cryopreserved. Before the experiment, 3-5 cryotubes of FE002-SK2 cells (passage 12; P12), which are fetal skin fibroblast cells, were thawed. Every cryotube contained $3\times10^6$ cells in 0.4 mL. The contents of all of the 3-5 cryotubes were combined and mixed.

For the DMEM group:

(1) 5-fold dilution: 20 μL cells were combined with 80 μL DMEM (cells diluted 5 folds). The number of post-thaw cells were counted.

(2) 12.5-fold dilution: 20 μL cells were combined with 230 μL DMEM (cells diluted 12.5 folds). The number of post-thaw cells were counted.

For the cell stabilizing medium (comprising gelatin) group:

(1) 5-fold dilution, 37° C.: 200 μL cells and 800 μL cell stabilizing medium (gelatin solution) were added to a 1.5-mL Eppendorf tube, and mixed. Cell viability was analyzed at time 0 (T0). The remaining test sample was incubated in a 37° C. water bath. Cell viability was analyzed again at the following time points: 2 hrs (T2), 4 hrs (T4) and 8 hrs (T8).

(2) 12.5-time dilution, 37° C.: 200 μL cells and 2300 μL gelatin solution were added to a 15-mL centrifuge tube, and mixed. Cell viability was analyzed at time 0 (T0). The remaining test sample was incubated in a 37° C. water bath. Cell viability was analyzed at the following times: time points: 2 hrs (T2), 4 hrs (T4) and 8 hrs (T8).

Similarly, cell viabilities were also tested for the 5-fold dilution and 12.5-fold dilution at 25° C.

TABLE 12

Cell viabilities after diluted with gelatin solutions at different folds (5X or 12.5X) and incubated at 25° C.

| | 5X dilution | Cell viability (%) (mean ± SD) | 12.5X dilution | Cell viability (%) (mean ± SD) |
|---|---|---|---|---|
| DMEM | T0 | 81 ± 0 | T0 | 78.5 ± 0.7 |
| Gelatin (1 wt %) | T0 | 80 ± 2.8 | T0 | 64.5 ± 0.7 |
| | T2 | 80.5 ± 0.7 | T2 | 63 ± 1.4 |
| | T4 | 76.5 ± 2.1 | T4 | 61.5 ± 2.1 |
| | T8 | 73 ± 1.4 | T8 | 57.5 ± 0.7 |
| Gelatin (3 wt %) | T0 | 80.5 ± 2.1 | T0 | 70 ± 1.4 |
| | T2 | 77.5 ± 2.1 | T2 | 60 ± 1.4 |
| | T4 | 78.5 ± 0.7 | T4 | 57 ± 1.4 |
| | T8 | 74.5 ± 0.7 | T8 | 45.5 ± 3.5 |
| Gelatin (17 wt %) | T0 | 74 ± 2.8 | T0 | 63.5 ± 0.7 |
| | T2 | 68 ± 0 | T2 | 64.5 ± 0.7 |
| | T4 | 64.5 ± 0.7 | T4 | 53.5 ± 2.1 |
| | T8 | 53 ± 5.7 | T8 | 50.5 ± 0.7 |

TABLE 13

Cell viabilities after diluted with gelatin solutions at different folds (5X or 12.5X) and incubated at 37° C.

| | 5X dilution | Cell viability (%) (mean ± SD) | 12.5X dilution | Cell viability (%) (mean ± SD) |
|---|---|---|---|---|
| DMEM | T0 | 81 ± 0 | T0 | 77.0 ± 0 |
| Gelatin (1 wt %) | T0 | 77.5 ± 3.5 | T0 | 71.0 ± 5.7 |
| | T2 | 78.0 ± 1.4 | T2 | 65.5 ± 0.7 |
| | T4 | 74.5 ± 3.5 | T4 | 54.5 ± 6.4 |
| | T8 | 62.5 ± 3.5 | T8 | 21.5 ± 2.1 |
| Gelatin (3 wt %) | T0 | 78.5 ± 3.5 | T0 | 73.5 ± 4.9 |
| | T2 | 76.0 ± 1.4 | T2 | 66.5 ± 0.7 |
| | T4 | 75 ± 1.4 | T4 | 49.0 ± 0 |
| | T8 | 65.0 ± 1.4 | T8 | 22.5 ± 9.2 |
| Gelatin (17 wt %) | T0 | 74.0 ± 0 | T0 | 69.0 ± 5.7 |
| | T2 | 72.0 ± 1.4 | T2 | 62.0 ± 0 |
| | T4 | 70 ± 1.4 | T4 | 58.5 ± 2.1 |
| | T8 | 53.5 ± 12.0 | T8 | 38.0 ± 1.4 |

TABLE 14

Cell viabilities after diluted with gelatin solutions at 5X and incubated at 25° C. (raw data)
25° C., Dilution factor: 5X

| | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| DMEM-1 (Dilute 5X) | 1.15E+06 | 2.09E+05 | 9.44E+05 | 81 | 81 | 0.0 | 81 ± 0 |
| DMEM-2 (Dilute 5X) | 1.16E+06 | 2.12E+05 | 9.52E+05 | 81 | | | |
| 1%-T0-1 | 1.25E+06 | 2.18E+05 | 1.03E+06 | 82 | 80 | 2.8 | 80 ± 2.8 |
| 1%-T0-2 | 1.10E+06 | 2.35E+05 | 8.71E+05 | 78 | | | |
| 3%-T0-1 | 1.28E+06 | 2.23E+05 | 1.06E+06 | 82 | 80.5 | 2.1 | 80.5 ± 2.1 |
| 3%-T0-2 | 1.22E+06 | 2.46E+05 | 9.82E+05 | 79 | | | |
| 17%-T0-1 | 1.26E+06 | 3.00E+05 | 9.61E+05 | 76 | 74 | 2.8 | 74 ± 2.8 |
| 17%-T0-2 | 1.21E+06 | 3.38E+05 | 8.77E+05 | 72 | | | |
| 1%-T2-1 | 1.20E+06 | 2.35E+05 | 9.68E+05 | 80 | 80.5 | 0.7 | 80.5 ± 0.7 |
| 1%-T2-2 | 1.18E+06 | 2.24E+05 | 9.58E+05 | 81 | | | |
| 3%-T2-1 | 1.11E+06 | 2.62E+05 | 8.50E+05 | 76 | 77.5 | 2.1 | 77.5 ± 2.1 |
| 3%-T2-2 | 1.13E+06 | 2.38E+05 | 9.01E+05 | 79 | | | |
| 17%-T2-1 | 1.12E+06 | 3.60E+05 | 7.67E+05 | 68 | 68 | 0.0 | 68 ± 0 |
| 17%-T2-2 | 1.14E+06 | 3.64E+05 | 7.76E+05 | 68 | | | |
| 1%-T4-1 | 1.13E+06 | 2.76E+05 | 8.54E+05 | 75 | 76.5 | 2.1 | 76.5 ± 2.1 |
| 1%-T4-2 | 1.12E+06 | 2.40E+05 | 8.87E+05 | 78 | | | |
| 3%-T4-1 | 1.20E+06 | 2.59E+05 | 9.49E+05 | 78 | 78.5 | 0.7 | 78.5 ± 0.7 |
| 3%-T4-2 | 1.30E+06 | 2.63E+05 | 1.03E+05 | 79 | | | |
| 17%-T4-1 | 1.23E+06 | 4.43E+05 | 7.91E+05 | 64 | 64.5 | 0.7 | 64.5 ± 0.7 |

TABLE 14-continued

Cell viabilities after diluted with gelatin solutions at 5X and incubated at 25° C. (raw data)
25° C., Dilution factor: 5X

| | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| 17%-T4-2 | 1.26E+06 | 4.40E+05 | 8.23E+05 | 65 | | | |
| 1%-T8-1 | 1.12E+06 | 2.88E+05 | 8.38E+05 | 74 | 73 | 1.4 | 73 ± 1.4 |
| 1%-T8-2 | 1.10E+06 | 3.00E+05 | 8.00E+05 | 72 | | | |
| 3%-T8-1 | 1.24E+06 | 3.07E+05 | 9.40E+05 | 75 | 74.5 | 0.7 | 74.5 ± 0.7 |
| 3%-T8-2 | 1.29E+06 | 3.30E+05 | 9.62E+05 | 74 | | | |
| 17%-T8-1 | 1.19E+06 | 6.08E+05 | 5.87E+05 | 49 | 53 | 5.7 | 53 ± 5.7 |
| 17%-T8-2 | 1.26E+06 | 5.44E+05 | 7.25E+05 | 57 | | | |

TABLE 15

Cell viabilities after diluted with gelatin solutions at 12.5X and incubated at 25° C. (raw data)
25° C., Dilution factor: 12.5X

| | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| DMEM-1 (Dilute 12.5X) | 4.45E+05 | 9.78E+04 | 3.47E+05 | 78 | 78.5 | 0.7 | 78.5 ± 0.7 |
| DMEM-2 (Dilute 12.5X) | 4.92E+05 | 1.02E+05 | 3.90E+05 | 79 | | | |
| 1%-T0-1 | 4.70E+05 | 1.69E+05 | 3.01E+05 | 64 | 64.5 | 0.7 | 64.5 ± 0.7 |
| 1%-T0-2 | 4.77E+05 | 1.65E+05 | 3.12E+05 | 65 | | | |
| 3%-T0-1 | 4.43E+05 | 1.36E+05 | 3.06E+05 | 69 | 70 | 1.4 | 70 ± 1.4 |
| 3%-T0-2 | 4.64E+05 | 1.32E+05 | 3.31E+05 | 71 | | | |
| 17%-T0-1 | 4.43E+05 | 1.61E+05 | 2.82E+05 | 63 | 63.5 | 0.7 | 63.5 ± 0.7 |
| 17%-T0-2 | 4.02E+05 | 1.41E+05 | 2.61E+05 | 64 | | | |
| 1%-T2-1 | 4.55E+05 | 1.69E+05 | 2.85E+05 | 62 | 63 | 1.4 | 63 ± 1.4 |
| 1%-T2-2 | 4.39E+05 | 1.58E+05 | 2.81E+05 | 64 | | | |
| 3%-T2-1 | 4.63E+05 | 1.86E+05 | 2.77E+05 | 59 | 60 | 1.4 | 60 ± 1.4 |
| 3%-T2-2 | 4.66E+05 | 1.80E+05 | 2.85E+05 | 61 | | | |
| 17%-T2-1 | 5.97E+05 | 2.04E+05 | 3.93E+05 | 65 | 64.5 | 0.7 | 64.5 ± 0.7 |
| 17%-T2-2 | 5.78E+05 | 2.04E+05 | 3.74E+05 | 64 | | | |
| 1%-T4-1 | 4.12E+05 | 1.49E+05 | 2.62E+05 | 63 | | 2.1 | 61.5 ± 2.1 |
| 1%-T4-2 | 3.79E+05 | 1.50E+05 | 2.29E+05 | 60 | 61.5 | | |
| 3%-T4-1 | 4.97E+05 | 2.05E+05 | 2.92E+05 | 58 | 57 | 1.4 | 57 ± 1.4 |
| 3%-T4-2 | 4.65E+05 | 2.02E+05 | 2.62E+05 | 56 | | | |
| 17%-T4-1 | 4.78E+05 | 2.29E+05 | 2.48E+05 | 52 | 53.5 | 2.1 | 53.5 ± 2.1 |
| 17%-T4-2 | 4.86E+05 | 2.16E+05 | 2.70E+05 | 55 | | | |
| 1%-T8-1 | 3.11E+05 | 1.30E+05 | 1.81E+05 | 58 | 57.5 | 0.7 | 57.5 ± 0.7 |
| 1%-T8-2 | 2.89E+05 | 1.23E+05 | 1.65E+05 | 57 | | | |
| 3%-T8-1 | 4.85E+05 | 2.49E+05 | 2.35E+05 | 48 | 45.5 | 3.5 | 45.5 ± 3.5 |
| 3%-T8-2 | 4.41E+05 | 2.47E+05 | 1.94E+05 | 43 | | | |
| 17%-T8-1 | 5.69E+05 | 2.79E+05 | 2.90E+05 | 50 | 50.5 | 0.7 | 50.5 ± 0.7 |
| 17%-T8-2 | 5.76E+05 | 2.81E+05 | 2.95E+05 | 51 | | | |

TABLE 16

Cell viabilities after diluted with gelatin solutions at 5X and incubated at 37° C. (raw data)
37° C., Dilution factor: 5X

| | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| DMEM-1 (Dilute 5X) | 1.30E+06 | 2.37E+05 | 1.06E+06 | 81 | 81 | 0.0 | 81.0 ± 0 |
| DMEM-2 (Dilute 5X) | 1.26E+06 | 2.36E+05 | 1.02E+06 | 81 | | | |
| 1%-T0-1 | 1.30E+06 | 2.50E+05 | 1.05E+06 | 80 | 77.5 | 3.5 | 77.5 ± 3.5 |
| 1%-T0-2 | 1.28E+06 | 3.09E+05 | 9.73E+05 | 75 | | | |

TABLE 16-continued

Cell viabilities after diluted with gelatin solutions at 5X and incubated at 37° C. (raw data)
37° C., Dilution factor: 5X

|  | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| 3%-T0-1 | 1.35E+06 | 2.50E+05 | 1.10E+06 | 81 | 78.5 | 3.5 | 78.5 ± 3.5 |
| 3%-T0-2 | 1.23E+06 | 2.85E+05 | 9.44E+05 | 76 | | | |
| 17%-T0-1 | 1.23E+06 | 3.15E+05 | 9.17E+05 | 74 | 74 | 0.0 | 74.0 ± 0 |
| 17%-T0-2 | 1.14E+06 | 2.88E+05 | 8.56E+05 | 74 | | | |
| 1%-T2-1 | 1.32E+06 | 3.03E+05 | 1.01E+06 | 77 | 78 | 1.4 | 78.0 ± 1.4 |
| 1%-T2-2 | 1.40E+06 | 2.88E+05 | 1.11E+06 | 79 | | | |
| 3%-T2-1 | 1.26E+06 | 3.15E+05 | 9.49E+05 | 75 | 76 | 1.4 | 76.0 ± 1.4 |
| 3%-T2-2 | 1.39E+06 | 3.07E+05 | 1.08E+06 | 77 | | | |
| 17%-T2-1 | 1.25E+06 | 3.61E+05 | 8.89E+05 | 71 | 72 | 1.4 | 72.0 ± 1.4 |
| 17%-T2-2 | 1.35E+06 | 3.53E+05 | 1.00E+06 | 73 | | | |
| 1%-T4-1 | 1.20E+06 | 3.31E+05 | 8.72E+05 | 72 | 74.5 | 3.5 | 74.5 ± 3.5 |
| 1%-T4-2 | 1.29E+06 | 2.92E+05 | 1.00E+06 | 77 | | | |
| 3%-T4-1 | 1.30E+06 | 3.05E+05 | 1.00E+06 | 76 | 75 | 1.4 | 75 ± 1.4 |
| 3%-T4-2 | 1.33E+06 | 3.42E+05 | 9.93E+05 | 74 | | | |
| 17%-T4-1 | 1.34E+06 | 4.06E+05 | 9.36E+05 | 69 | 70 | 1.4 | 70 ± 1.4 |
| 17%-T4-2 | 1.44E+06 | 4.09E+05 | 1.03E+06 | 71 | | | |
| 1%-T8-1 | 1.17E+06 | 4.01E+05 | 7.69E+05 | 65 | 62.5 | 3.5 | 62.5 ± 3.5 |
| 1%-T8-2 | 1.07E+06 | 4.26E+05 | 6.43E+05 | 60 | | | |
| 3%-T8-1 | 1.38E+06 | 4.97E+05 | 8.86E+05 | 64 | 65 | 1.4 | 65.0 ± 1.4 |
| 3%-T8-2 | 1.41E+06 | 4.74E+05 | 9.35E+05 | 66 | | | |
| 17%-T8-1 | 1.31E+06 | 7.15E+05 | 5.98E+05 | 45 | 53.5 | 12.0 | 53.5 ± 12.0 |
| 17%-T8-2 | 8.36E+05 | 3.17E+05 | 5.19E+05 | 62 | | | |

TABLE 17

Cell viabilities after diluted with gelatin solutions at 12.5X and incubated at 37° C. (raw data)
37° C., Dilution factor: 12.5X

|  | Total cells (cells/mL) | Non-viable cells (cells/mL) | Viable cells (cells/mL) | Cell viability (%) | Average viability (%) | SD | Cell viability (%) (mean ± SD) |
|---|---|---|---|---|---|---|---|
| DMEM-1 (Dilute 5X) | 4.75E+05 | 1.08E+05 | 3.67E+05 | 77 | 77 | 0.0 | 77.0 ± 0 |
| DMEM-2 (Dilute 5X) | 4.92E+05 | 1.09E+05 | 3.82E+05 | 77 | | | |
| 1%-T0-1 | 4.71E+05 | 1.17E+05 | 3.53E+05 | 75 | 71 | 5.7 | 71.0 ± 5.7 |
| 1%-T0-2 | 4.64E+05 | 1.50E+05 | 3.13E+05 | 67 | | | |
| 3%-T0-1 | 4.82E+05 | 1.06E+05 | 3.76E+05 | 77 | 73.5 | 4.9 | 73.5 ± 4.9 |
| 3%-T0-2 | 4.42E+05 | 1.31E+05 | 3.11E+05 | 70 | | | |
| 17%-T0-1 | 4.43E+05 | 1.54E+05 | 2.89E+05 | 65 | 69 | 5.7 | 69.0 ± 5.7 |
| 17%-T0-2 | 4.66E+05 | 1.22E+05 | 3.43E+05 | 73 | | | |
| 1%-T2-1 | 4.26E+05 | 1.47E+05 | 2.78E+05 | 65 | 65.5 | 0.7 | 65.5 ± 0.7 |
| 1%-T2-2 | 4.25E+05 | 1.43E+05 | 2.81E+05 | 66 | | | |
| 3%-T2-1 | 4.77E+05 | 1.55E+05 | 3.21E+05 | 67 | 66.5 | 0.7 | 66.5 ± 0.7 |
| 3%-T2-2 | 4.50E+05 | 1.48E+05 | 3.01E+05 | 66 | | | |
| 17%-T2-1 | 4.06E+05 | 1.53E+05 | 2.53E+05 | 62 | 62 | 0.0 | 62.0 ± 0 |
| 17%-T2-2 | 4.08E+05 | 1.51E+05 | 2.56E+05 | 62 | | | |
| 1%-T4-1 | 3.99E+05 | 1.63E+05 | 2.35E+05 | 59 | 54.5 | 6.4 | 54.5 ± 6.4 |
| 1%-T4-2 | 3.50E+05 | 1.73E+05 | 1.77E+05 | 50 | | | |
| 3%-T4-1 | 4.49E+05 | 2.27E+05 | 2.22E+05 | 49 | 49 | 0.0 | 49.0 ± 0 |
| 3%-T4-2 | 4.85E+05 | 2.43E+05 | 2.42E+05 | 49 | | | |
| 17%-T4-1 | 4.30E+05 | 1.71E+05 | 2.59E+05 | 60 | 58.5 | 2.1 | 58.5 ± 2.1 |
| 17%-T4-2 | 4.13E+05 | 1.76E+05 | 2.36E+05 | 57 | | | |
| 1%-T8-1 | 2.99E+05 | 2.30E+05 | 6.91E+04 | 23 | 21.5 | 2.1 | 21.5 ± 2.1 |
| 1%-T8-2 | 2.69E+05 | 2.14E+05 | 5.56E+04 | 20 | | | |
| 3%-T8-1 | 4.30E+05 | 3.04E+05 | 1.26E+05 | 29 | 22.5 | 9.2 | 22.5 ± 9.2 |
| 3%-T8-2 | 4.57E+05 | 3.08E+05 | 7.71E+04 | 16 | | | |
| 17%-T8-1 | 3.20E+05 | 1.99E+05 | 1.21E+05 | 37 | 38 | 1.4 | 38.0 ± 1.4 |
| 17%-T8-2 | 3.72E+05 | 2.26E+05 | 1.45E+05 | 39 | | | |

Discussion

The results show that the post-thaw cell viability was higher when incubated with the cell stabilizing medium comprising 1 wt %, 3 wt % or 17 wt % of gelatin, compared to DMEM. At 25° C. or 37° C., the cells diluted 5-fold with the cell stabilizing medium exhibited a higher and prolonged viability compared to the cells diluted 12.5-fold with the cell stabilizing medium.

Example 3 Effects of Working Gelatin Concentrations on Cell Viabilities

Figure 2:
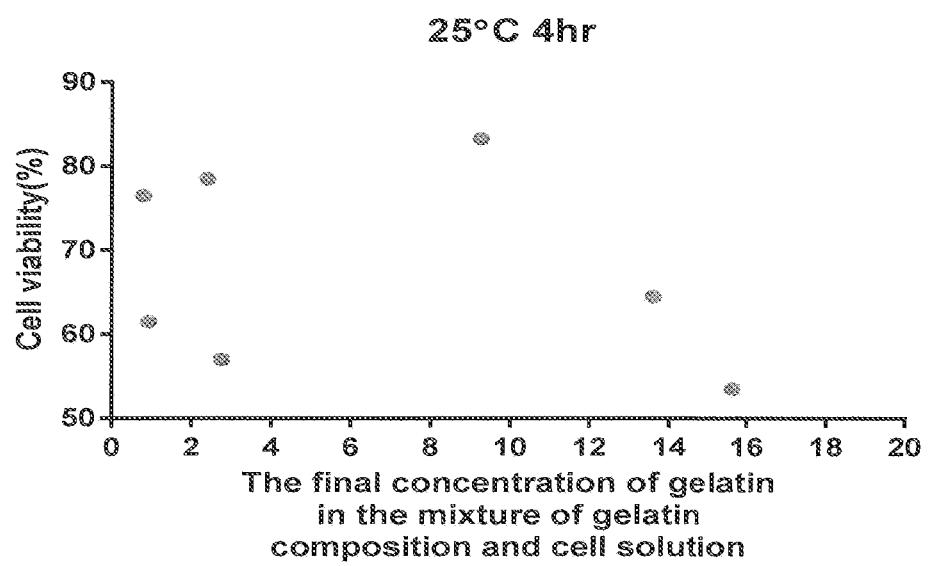
FIG. 2 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. The mixture was incubated at 25° C. for 4 hours before post-thaw cell viabilities were assayed.
Figure 3:
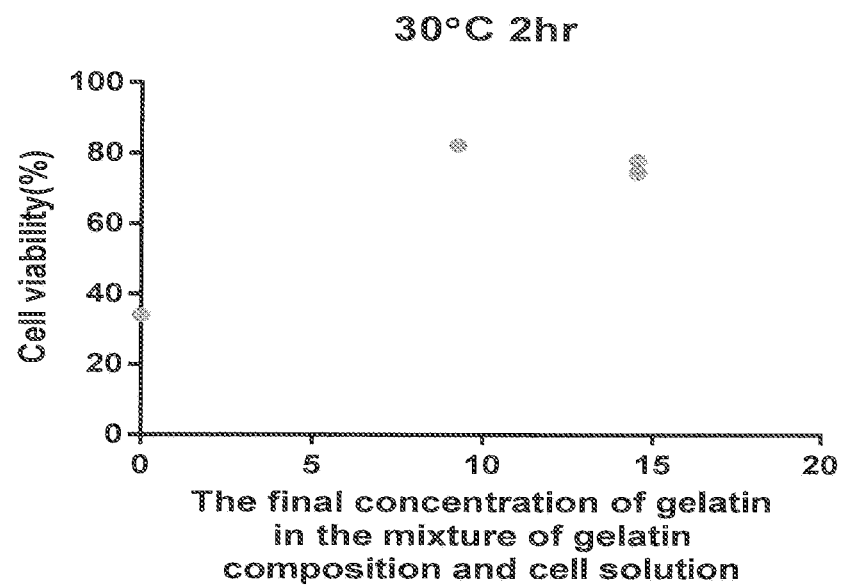
FIG. 3 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. In control samples, the thawed cell suspension (in the freezing solution) and DMEM was mixed. The mixture was incubated at 30° C. for 2 hours before post-thaw cell viabilities were assayed.
Figure 4:
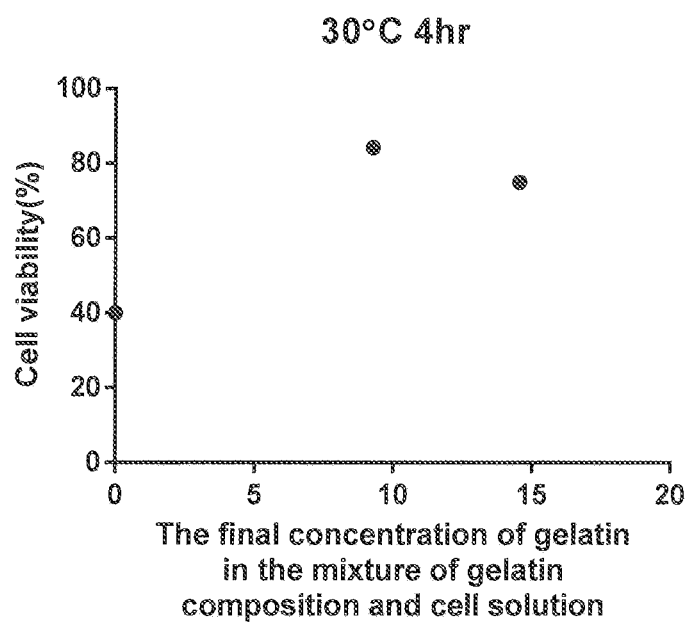
FIG. 4 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. In control samples, the thawed cell suspension (in the freezing solution) and DMEM was mixed. The mixture was incubated at 30° C. for 4 hours before post-thaw cell viabilities were assayed.
Figure 5:
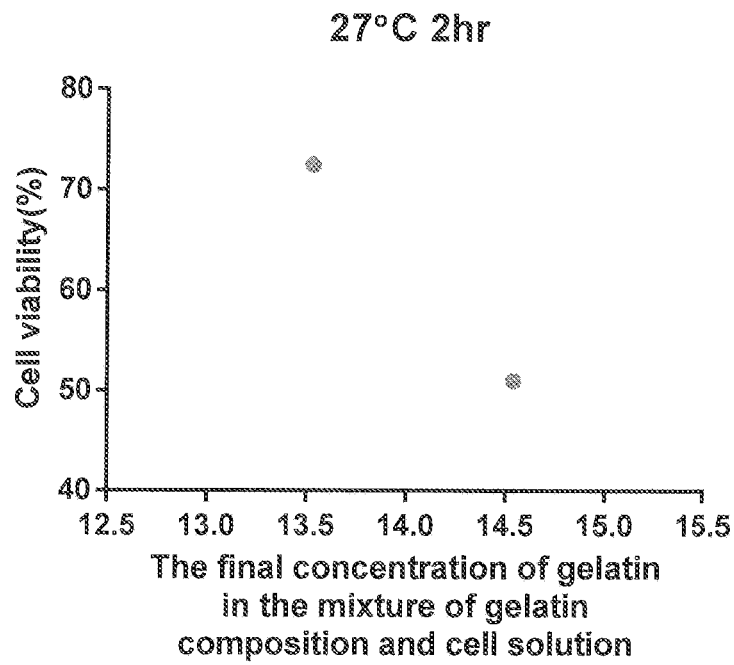
FIG. 5 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. The mixture was incubated at 27° C. for 2 hours before post-thaw cell viabilities were assayed.
Figure 6:
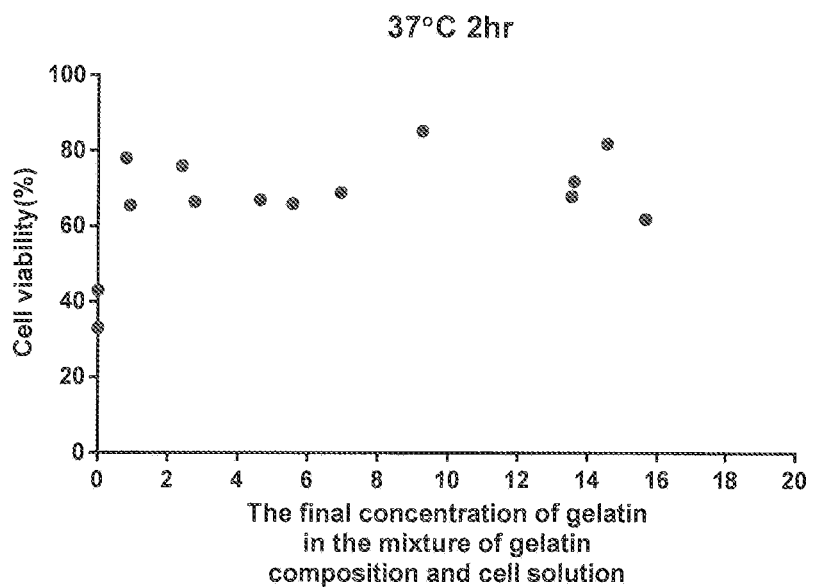
FIG. 6 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. In control samples, the thawed cell suspension (in the freezing solution) and DMEM was mixed. The mixture was incubated at 37° C. for 2 hours before post-thaw cell viabilities were assayed.
Figure 7:
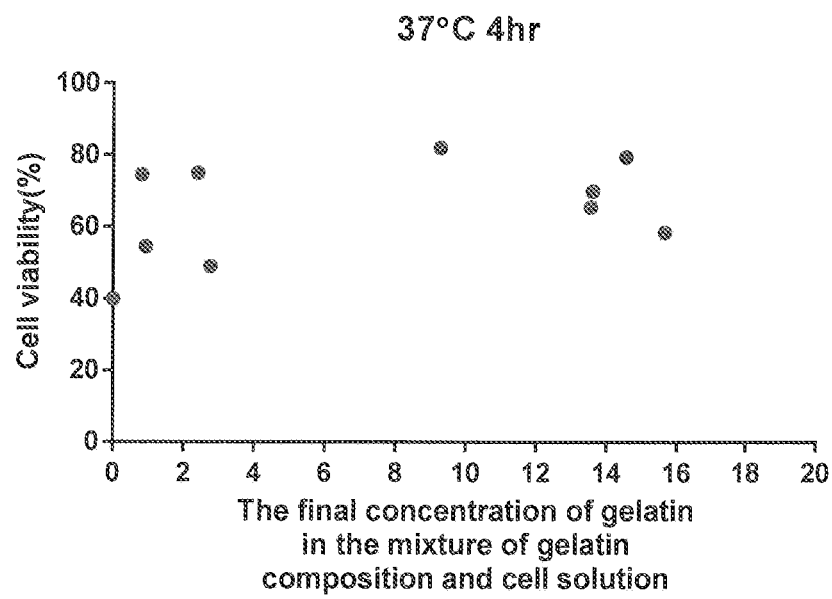
FIG. 7 is a graph showing the effects of gelatin concentration and incubation temperature and time on post-thaw cell viabilities. In the experiment, the cells were initially frozen in the glycerol-based freezing solution. The thawed cell suspension (in the freezing solution) and a cell stabilizing medium containing gelatin were mixed. In control samples, the thawed cell suspension (in the freezing solution) and DMEM was mixed. The mixture was incubated at 37° C. for 4 hours before post-thaw cell viabilities were assayed.
Figure 8:
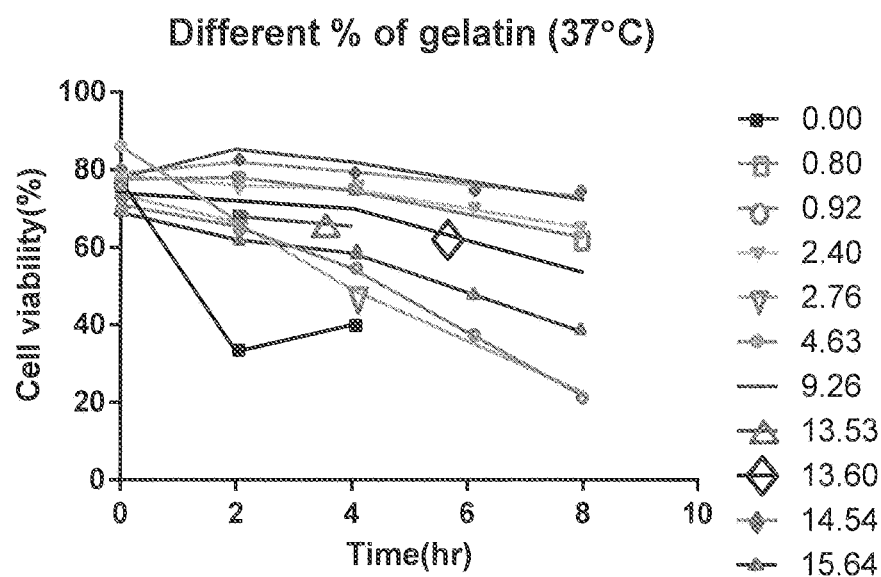
FIG. 8 is a graph showing the effects of gelatin concentration and incubation time on post-thaw cell viabilities. In the experiment, the cells were initially frozen in the glycerol-based freezing solution. The thawed cell suspension (in the freezing solution) and a cell stabilizing medium containing gelatin were mixed. In control samples, the thawed cell suspension (in the freezing solution) and DMEM was mixed. The mixture was incubated at 37° C. before post-thaw cell viabilities were assayed.
Figure 9:
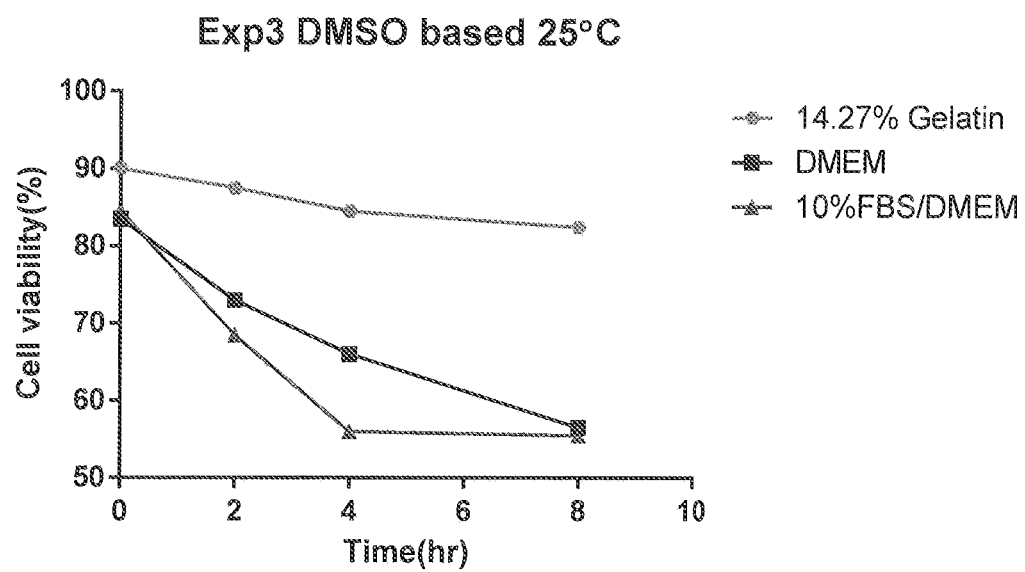
FIG. 9 is a graph showing the effects of gelatin and incubation time on post-thaw cell viabilities. In the experiment, the cells were initially frozen in the DMSO-based freezing solution. The thawed cell suspension (in the freezing solution) and a cell stabilizing medium containing gelatin were mixed. In control samples, the thawed cell suspension (in the freezing solution) and either DMEM, or 10% FBS/DMEM, was mixed. The mixture was incubated at 25° C. before post-thaw cell viabilities were assayed.

Table 18 and FIGS. 1-9 show the effects of the working concentrations of gelatin on the cell viabilities, based on the data of Experiment Nos. 1-10 ("Exp. 1" to "Exp. 10") in Example 1 and Example 2.

TABLE 18

| | Working concentration of gelatin in the mixture of cell stabilizing medium (gelatin composition) and cell suspension (wt %) | Incubation temperature of mixture of gelatin composition and cell suspension (° C.) | Incubation time (hour) | Cell viability |
|---|---|---|---|---|
| Exp. 1 | 14.54% | 37 | 0 | 79.0% |
| | (DMEM only) 0% | 37 | 0 | 77.0% |
| | 14.54% | 30 | 2 | 78.0% |
| | (DMEM only) 0% | 30 | 2 | 34.0% |
| | 14.54% | 37 | 2 | 82.0% |
| | (DMEM only) 0% | 37 | 2 | 33.0% |
| | 14.54% | 30 | 4 | 75.0% |
| | (DMEM only) 0% | 30 | 4 | 40.0% |
| | 14.54% | 37 | 4 | 76.0% |
| | (DMEM only) 0% | 37 | 4 | 40.0% |
| Exp. 2 | 14.54% | 37 | 0 | 78.0% |
| | 14.54% | 37 | 1 | 80.0% |
| | 14.54% | 37 | 2 | 78.0% |
| | 14.54% | 37 | 4 | 79.5% |
| | 14.54% | 37 | 8 | 73.0% |
| | 14.54% | 37 | 24 | 38.5% |
| Exp. 3 (CPA was DMSO) | 14.27% | 25 | 0 | 90.0% |
| | (DMEM only) 0% | 25 | 0 | 83.5% |
| | (10% FBS/DMEM) 0% | 25 | 0 | 84.5% |
| | 14.27% | 25 | 2 | 87.5% |
| | (DMEM only) 0% | 25 | 2 | 73.0% |
| | (10% FBS/DMEM) 0% | 25 | 2 | 68.5% |
| | 14.27% | 25 | 4 | 84.5% |
| | (DMEM only) 0% | 25 | 4 | 66.0% |
| | (10% FBS/DMEM) 0% | 25 | 4 | 56.0% |
| | 14.27% | 25 | 8 | 82.5% |
| | (DMEM only) 0% | 25 | 8 | 56.5% |
| | (10% FBS/DMEM) 0% | 25 | 8 | 55.5% |
| Exp. 4 | 9.26% | 37 | 0 | 78.0% |
| | 9.26% | 37 | 2 | 85.3% |
| | 9.26% | 37 | 4 | 82.0% |
| | 9.26% | 37 | 6 | 81.7% |
| | 9.26% | 37 | 8 | 72.3% |
| | 9.26% | 37 | 24 | 29.0% |
| Exp. 5 | 9.26% | 25 | 0 | 74.5% |
| | 9.26% | 30 | 0 | 74.5% |
| | 9.26% | 25 | 2 | 81.0% |
| | 9.26% | 30 | 2 | 82.3% |
| | 9.26% | 25 | 4 | 83.3% |
| | 9.26% | 30 | 4 | 84.3% |
| | 9.26% | 25 | 6 | 84.0% |
| | 9.26% | 30 | 6 | 83.0% |
| | 9.26% | 25 | 8 | 86.0% |
| | 9.26% | 30 | 8 | 82.3% |
| | 9.26% | 25 | 24 | 84.0% |
| | 9.26% | 30 | 24 | 77.3% |
| | 9.26% | 25 | 72 | 51.5% |
| | 9.26% | 30 | 72 | 11.5% |
| Exp. 6 | 4.63% | 37 | 0 | 86.0% |
| | (DMEM only) 0% | 37 | 0 | 67.5% |
| | 4.63% | 37 | 2 | 67.0% |
| | (DMEM only) 0% | 37 | 2 | 43.0% |
| Exp. 7 | 5.56% | 37 | 0 | 86.0% |
| | (DMEM only) 0% | 37 | 0 | 67.5% |
| | 5.56% | 37 | 2 | 66.0% |
| | (DMEM only) 0% | 37 | 2 | 43.0% |
| Exp. 8 | 6.94% | 37 | 0 | 86.0% |
| | (DMEM only) 0% | 37 | 0 | 67.5% |
| | 6.94% | 37 | 2 | 69.0% |
| | (DMEM only) 0% | 37 | 2 | 43.0% |
| Exp. 9 | 13.53% | 37 | 0 | 66.0% |
| | 13.53% | 27 | 2 | 72.5% |
| | 13.53% | 37 | 2 | 68.0% |
| | 13.53% | 28 | 4 | 73.0% |
| | 13.53% | 37 | 4 | 65.5% |
| Exp. 10 | 14.54% | 23 | 1 | 54.0% |
| | 14.54% | 27 | 1 | 68.0% |
| | 14.54% | 30 | 1 | 75.5% |
| | 14.54% | 23 | 2 | 37.0% |
| | 14.54% | 27 | 2 | 51.0% |
| | 14.54% | 30 | 2 | 74.5% |
| Example 2 (Table 14) | (DMEM only) 0% | 25 | 0 | 81.0% |
| | 0.80% | 25 | 0 | 80.0% |
| | 0.80% | 25 | 2 | 80.5% |
| | 0.80% | 25 | 4 | 76.5% |
| | 0.80% | 25 | 8 | 73.0% |
| | 2.40% | 25 | 0 | 80.5% |
| | 2.40% | 25 | 2 | 77.5% |
| | 2.40% | 25 | 4 | 78.5% |
| | 2.40% | 25 | 8 | 74.5% |
| | 13.60% | 25 | 0 | 74.0% |
| | 13.60% | 25 | 2 | 68.0% |
| | 13.60% | 25 | 4 | 64.5% |
| | 13.60% | 25 | 8 | 53.0% |
| Example 2 (Table 15) | (DMEM only) 0% | 25 | 0 | 78.5% |
| | 0.92% | 25 | 0 | 64.5% |
| | 0.92% | 25 | 2 | 63.0% |
| | 0.92% | 25 | 4 | 61.5% |
| | 0.92% | 25 | 8 | 57.5% |
| | 2.76% | 25 | 0 | 70.0% |
| | 2.76% | 25 | 2 | 60.0% |
| | 2.76% | 25 | 4 | 57.0% |
| | 2.76% | 25 | 8 | 45.5% |
| | 15.64% | 25 | 0 | 63.5% |
| | 15.64% | 25 | 2 | 64.5% |
| | 15.64% | 25 | 4 | 53.5% |
| | 15.64% | 25 | 8 | 50.5% |
| Example 2 (Table 16) | (DMEM only) 0% | 37 | 0 | 81.0% |
| | 0.80% | 37 | 0 | 77.5% |
| | 0.80% | 37 | 2 | 78.0% |
| | 0.80% | 37 | 4 | 74.5% |
| | 0.80% | 37 | 8 | 62.5% |
| | 2.40% | 37 | 0 | 78.5% |
| | 2.40% | 37 | 2 | 76.0% |
| | 2.40% | 37 | 4 | 75.0% |
| | 2.40% | 37 | 8 | 65.0% |
| | 13.60% | 37 | 0 | 74.0% |
| | 13.60% | 37 | 2 | 72.0% |
| | 13.60% | 37 | 4 | 70.0% |
| | 13.60% | 37 | 8 | 53.5% |
| Example 2 (Table 17) | (DMEM only) 0% | 37 | 0 | 77.0% |
| | 0.92% | 37 | 0 | 71.0% |
| | 0.92% | 37 | 2 | 65.5% |
| | 0.92% | 37 | 4 | 54.5% |
| | 0.92% | 37 | 8 | 21.5% |
| | 2.76% | 37 | 0 | 73.5% |
| | 2.76% | 37 | 2 | 66.5% |
| | 2.76% | 37 | 4 | 49.0% |
| | 2.76% | 37 | 8 | 22.5% |
| | 15.64% | 37 | 0 | 69.0% |

TABLE 18-continued

| Working concentration of gelatin in the mixture of cell stabilizing medium (gelatin composition) and cell suspension (wt %) | Incubation temperature of mixture of gelatin composition and cell suspension (° C.) | Incubation time (hour) | Cell viability |
|---|---|---|---|
| 15.64% | 37 | 2 | 62.0% |
| 15.64% | 37 | 4 | 58.5% |
| 15.64% | 37 | 8 | 38.0% |

Example 4 Comparison Between Gelatin-Based Solution and Other Solutions for Maintaining Cell Viability after Thawing Materials ADAM Accuchip and ADAM Solution were from NanoEnTek. DMEM and fetal bovine serum (FBS) were from Gibco. Bovine serum albumin was from Sigma.

Testing solutions (cell stabilizing medium, DMEM, or FBS) include:

Solution A ("Soln A"): DMEM

Solution B ("Soln B"): Gelatin 10 wt % in DMEM

Solution C ("Soln C"): Albumin 5 wt % in DMEM

Solution D ("Soln D"): Albumin 10 wt % in DMEM

Solution E ("Soln E"): Albumin 15.7 wt % in DMEM

Solution F ("Soln F"): FBS

Fibroblast cells (FE002-SK2) were frozen in a cryopreservation composition comprising glycerol at the concentration of $7.5 \times 10^6$ cells/mL.

1150 μL of each of testing solutions A-F were dispensed into 2-mL Eppendorf tubes, with 3 tubes for each solution.

The cryopreserved fibroblast cells were thawed in a 37° C. water bath. All cell suspensions were pooled into one tube. 100 μL thawed cell suspension was added to each of the Eppendorf tubes containing 1150 μL of the testing solution to form a mixture. The volume ratio of the testing solutions (cell stabilizing medium, or DMEM, or FBS) to the cell suspension is 11.5.

The mixture was incubated at 37° C. for 2 hours. Samples for each condition were triplicated. The total number of the cells, the number of the live cells and the number of the dead cells were assayed by using ADAM-MC Automatic Cell Counter (Digital Bio). Viability of the cells was calculated by the following formula: [(live cell number)/(total cell number)]×100%.

As shown in Table 19, after being incubated at 37° C. for 2 hours, the viability of the cells in the cell stabilizing medium comprising gelatin was about 77.3%. The viabilities of the cells in the cell stabilizing medium comprising 5 wt %, 10 wt %, or 15.7 wt % albumin were about 48.7%, 49.7% and 60.7%, respectively. Gelatin-based solution was able to maintain thawed cell viability better than other tested solutions.

TABLE 19

Viability of cells mixed with various testing solutions
Incubation Time = 2 h

| Testing Solution | # | Total cells (cells/mL) | Non-viable cells (cells/mL) | Viable cells (cells/mL) | Cell Viability (%) | Cell Viability (%) mean | SD |
|---|---|---|---|---|---|---|---|
| Soln A (DMEM) | 1 | 2.29E5 | 1.36E5 | 9.24E4 | 40 | 40.0 | 6.0 |
| | 2 | 2.12E5 | 1.38E5 | 7.38E4 | 34 | | |
| | 3 | 2.35E5 | 1.26E5 | 1.08E5 | 46 | | |
| Soln B (10 wt % Gelatin in DMEM) | 1 | 4.29E5 | 1.02E5 | 3.27E5 | 76 | 77.3 | 1.5 |
| | 2 | 4.30E5 | 8.93E4 | 3.40E5 | 79 | | |
| | 3 | 4.53E5 | 1.03E5 | 3.50E5 | 77 | | |
| Soln C (5 wt % Albumin in DMEM) | 1 | 2.59E5 | 1.19E5 | 1.39E5 | 53 | 48.7 | 7.5 |
| | 2 | 2.97E5 | 1.37E5 | 1.59E5 | 53 | | |
| | 3 | 2.53E5 | 1.49E5 | 1.03E5 | 40 | | |
| Soln D (10 wt % Albumin in DMEM) | 1 | 2.44E5 | 1.21E5 | 1.23E5 | 50 | 49.7 | 2.5 |
| | 2 | 2.47E5 | 1.17E5 | 1.29E5 | 52 | | |
| | 3 | 2.23E5 | 1.17E5 | 1.05E5 | 47 | | |
| Soln E (15.7 wt % Albumin in DMEM) | 1 | 2.39E5 | 1.07E5 | 1.31E5 | 55 | 60.7 | 5.1 |
| | 2 | 2.56E5 | 8.91E4 | 1.67E5 | 65 | | |
| | 3 | 2.57E5 | 9.74E4 | 1.59E5 | 62 | | |
| Soln F (PBS) | 1 | 3.96E5 | 1.57E5 | 2.38E5 | 60 | 60.7 | 3.1 |
| | 2 | 4.51E5 | 1.61E5 | 2.89E5 | 64 | | |
| | 3 | 4.10E5 | 1.70E5 | 2.40E5 | 58 | | |

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description is offered by way of illustration only and not as a limitation.

What is claimed is:

1. A method for maintaining cell viability, the method comprising the step of:
    mixing a cell suspension comprising one or more mammalian cells in a cryopreservation composition comprising glycerol which has been thawed from a cryopreserved state with a cell stabilizing medium to form a mixture,
    wherein the cell stabilizing medium is a thermoreversible hydrogel in a liquid state when mixed with the cell suspension that has been thawed and comprises about 0.8 wt % to about 15.7 wt % of gelatin based on the total weight of the mixture; and
    wherein the volume ratio of the cell stabilizing medium to the cell suspension ranges from about 3.0 to about 12.5.

2. The method of claim 1, wherein the mixture comprises about 2.4 wt % to about 7 wt % of gelatin.

3. The method of claim 1, wherein the mixture comprises about 9.3 wt % to about 14.6 wt % of gelatin.

4. The method of claim 1, wherein the volume ratio of the cell stabilizing medium to the cell suspension ranges from about 5 to about 10.

5. The method of claim 1, wherein the cells are in the cell suspension at a concentration ranging from about $7.5 \times 10^5$ cells/ml to about $7.5 \times 10^7$ cells/ml.

6. The method of claim 1, wherein the cryopreserved state is at a temperature ranging from about −70° C. and −200° C.

7. The method of claim 1, wherein the cells have a post-thaw viability of at least 70%.

8. The method of claim 1, wherein the cells have a post-thaw viability of at least 80%.

9. The method of claim 1, further comprising placing the cell stabilizing medium at a temperature ranging from about 25° C. to about 37° C. before the mixing step.

10. The method of claim 1, wherein gelatin has a weight average molecular mass ranging from about 100 kilodalton (kD) to about 200 kD.

11. The method of claim 1, wherein gelatin comprises denatured collagen.

12. The method of claim 1, wherein the cell stabilizing medium has a bloom value ranging from about 190 to about 325.

13. The method of claim 1, wherein the cells are human, porcine, canine, equine or bovine cells.

14. The method of claim 1, wherein the cells comprise tumor cells.

15. The method of claim 1, wherein the cells comprise fibroblasts.

16. The method of claim 1, wherein the cells comprise stem cells.

17. The method of claim 1, wherein the cells are present in the mixture at a concentration ranging from about $10^5$ cells/ml to about $10^7$ cells/ml.

18. The method of claim 1, wherein the cell stabilizing medium further comprises an amino acid, a cytokine, a lipid, a growth factor, an antibiotic, an antimycotic, a steroid hormone, a protein hormone, or a combination thereof.

19. A composition comprising
a cell suspension comprising one or more mammalian cells in a cryopreservation composition comprising glycerol which has been thawed from a cryopreserved state; and
a cell stabilizing medium wherein the cell stabilizing medium is a thermoreversible hydrogel in a liquid state when combined with the cell suspension that has been thawed;
wherein the composition comprises about 0.8 wt % to about 15.7 wt % of gelatin based on the total weight of the composition; and
wherein the volume ratio of the cell stabilizing medium to the cell suspension ranges from about 3.0 to about 12.5.

20. The composition of claim 19, comprising about 2.4 wt % to about 7 wt % of gelatin.

21. The composition of claim 19, comprising about 9.3 wt % to about 14.6 wt % of gelatin.

22. The composition of claim 19, wherein the cells have a post-thaw viability of at least 70%.

23. The composition of claim 19, wherein the gelatin has a weight average molecular mass ranging from about 100 kilodalton (kD) to about 200 kD.

24. The composition of claim 19, wherein the gelatin comprises denatured collagen.

25. The composition of claim 19, wherein the cells are human, porcine, canine, equine or bovine cells.

26. The composition of claim 19, wherein the cells comprise tumor cells.

27. The composition of claim 19, wherein the cells comprise fibroblasts.

28. The composition of claim 19, wherein the cells comprise stem cells.

29. A kit comprising the composition of claim 19.

30. The composition of claim 19, wherein the cells are present at a concentration ranging from about $10^5$ cells/ml to about $10^7$ cells/ml.

31. The composition of claim 19, wherein the cells are present at a concentration of about $7.5 \times 10^5$ cells/ml to about $7.5 \times 10^7$ cells/ml.

32. The composition of claim 19, wherein the cells have a post-thaw viability of at least 80%.

33. The composition of claim 19, wherein the volume ratio of the cell stabilizing medium to the cell suspension ranges from about 5 to about 10.

34. The composition of claim 19, wherein the volume ratio of the cell stabilizing medium to the cell suspension ranges from about 6.25 to about 12.5.

35. A composition comprising
a cell suspension comprising one or more mammalian cells in a cryopreservation composition comprising glycerol which has been thawed from a cryopreserved state; and
a cell stabilizing medium;
wherein the cell stabilizing medium is a thermoreversible hydrogel in a liquid state when combined with the cell suspension that has been thawed and comprises about 0.8 wt % to about 15.7 wt % of gelatin based on the total weight of the cell stabilizing medium; and
wherein the volume ratio of the cell stabilizing medium to the cell suspension ranges from about 3.0 to about 12.5.

36. The composition of claim 35, wherein the cell stabilizing medium comprises about 5.0 wt % to about 15.7 wt % of gelatin.

37. The composition of claim 35, wherein the cells have a post-thaw viability of at least 70%.

38. The composition of claim 35, wherein the cells have a post-thaw viability of at least 80%.

39. The composition of claim 35, wherein the gelatin has a weight average molecular mass ranging from about 100 kilodalton (kD) to about 200 kD.

40. The composition of claim 35, wherein the gelatin comprises denatured collagen.

41. The composition of claim 35, wherein the cells are human, porcine, canine, equine or bovine cells.

42. The composition of claim 35, wherein the cells comprise tumor cells.

43. The composition of claim 35, wherein the cells comprise fibroblasts.

44. The composition of claim 35, wherein the cells comprise stem cells.

45. The composition of claim 35, wherein the cells are present at a concentration ranging from about $10^5$ cells/ml to about $10^7$ cells/ml.

46. The composition of claim 35, wherein the cells are present at a concentration of about $7.5 \times 10^5$ cells/ml to about $7.5 \times 10^7$ cells/ml.

47. The composition of claim 35, wherein the volume ratio of the cell stabilizing medium to the cell suspension ranges from about 5 to about 10.

48. The composition of claim 35, wherein the volume ratio of the cell stabilizing medium to the cell suspension ranges from about 6.25 to about 12.5.

49. A kit comprising the composition of claim 35.

50. The method of claim 1, wherein the volume ratio of the cell stabilizing medium to the cell suspension ranges from about 6.25 to about 12.5.

* * * * *